US012068067B2

(12) United States Patent
Budz et al.

(10) Patent No.: US 12,068,067 B2
(45) Date of Patent: Aug. 20, 2024

(54) METHOD FOR USE IN GENERATING A COMPUTER-BASED VISUALIZATION OF 3D MEDICAL IMAGE DATA

(71) Applicant: Siemens Healthineers AG, Forchheim (DE)

(72) Inventors: Sebastian Budz, Erlangen (DE); Robert Schneider, Rosstal (DE); Stefan Thesen, Dormitz (DE)

(73) Assignee: Siemens Healthineers AG, Forchheim (DE)

( * ) Notice: Subject to any disclaimer, the term of this patent is extended or adjusted under 35 U.S.C. 154(b) by 321 days.

(21) Appl. No.: 17/495,890

(22) Filed: Oct. 7, 2021

(65) Prior Publication Data

US 2022/0122717 A1 Apr. 21, 2022

(30) Foreign Application Priority Data

Oct. 21, 2020 (DE) ................. 10 2020 213 305.0
Aug. 26, 2021 (EP) ..................... 21193309

(51) Int. Cl.
*G06T 7/00* (2017.01)
*G06T 7/11* (2017.01)
(Continued)

(52) U.S. Cl.
CPC .......... *G16H 30/20* (2018.01); *G06T 7/0014* (2013.01); *G06T 7/11* (2017.01); *G06T 19/00* (2013.01);
(Continued)

(58) Field of Classification Search
CPC ........ G16H 30/20; G16H 30/40; G16H 80/00; G06T 7/0014; G06T 7/11; G06T 19/00;
(Continued)

(56) References Cited

U.S. PATENT DOCUMENTS

2007/0248265 A1* 10/2007 Lundstrom ............. G06T 15/08
382/128
2009/0002366 A1* 1/2009 Kanitsar ................. G06T 15/08
345/419
(Continued)

FOREIGN PATENT DOCUMENTS

EP 3178068 B1 9/2018

OTHER PUBLICATIONS

Levoy M. et al.: "Display of Surfaces from Volume Data", IEEE Computer Graphics an Applications, Bd. 8, Nr. 3, 1988, Seiten 29-37; Marc Levoy.
(Continued)

*Primary Examiner* — Ping Y Hsieh
(74) *Attorney, Agent, or Firm* — Harness, Dickey & Pierce, P.L.C.

(57) ABSTRACT

A method for use in generating a computer-based visualization of 3D medical image data is described. The method includes receiving 3D medical image data and performing a selection process to select first image data forming a first portion of the 3D medical image data, the first image data representing a first anatomical object of a given type. An analysis process is performed on the first image data, a parameter of the analysis process being based on the given type of the first anatomical object. Based at least in part on a result of the analysis process, a visual parameter mapping for the first portion is determined, for use in a rendering process for generating a visualization of the 3D medical image data. Also described is a method of generating a computer-based visualization of 3D medical image data and an apparatus for performing the methods.

27 Claims, 6 Drawing Sheets

(51) Int. Cl.
  *G06T 19/00* (2011.01)
  *G16H 30/20* (2018.01)
  *G16H 30/40* (2018.01)
  *G16H 80/00* (2018.01)

(52) U.S. Cl.
  CPC ............ *G16H 30/40* (2018.01); *G16H 80/00* (2018.01); *G06T 2207/30004* (2013.01); *G06T 2210/41* (2013.01)

(58) Field of Classification Search
  CPC ....... G06T 2207/30004; G06T 2210/41; G06T 2207/10081; G06T 7/0012; G06T 15/08; G06T 17/00; G06T 19/20; H05K 2201/10272; H05K 1/0209
  See application file for complete search history.

(56) References Cited

U.S. PATENT DOCUMENTS

| | | | | |
|---|---|---|---|---|
| 2009/0129661 | A1* | 5/2009 | Licato | G06V 10/457 382/134 |
| 2014/0111508 | A1* | 4/2014 | Bystrov | G06T 15/00 345/419 |
| 2017/0294042 | A1* | 10/2017 | Engel | G06T 15/08 |
| 2019/0156526 | A1* | 5/2019 | Liu | G06T 7/0012 |

OTHER PUBLICATIONS

Kajiya et al.: "The rendering equation", ACM SIGGRAPH Computer Graphics, vol. 20, No. 4, Aug. 1986, pp. 143-150).

\* cited by examiner

METHOD FOR USE IN GENERATING A COMPUTER-BASED VISUALIZATION OF 3D MEDICAL IMAGE DATA

PRIORITY STATEMENT

The present application hereby claims priority under 35 U.S.C. § 119 to German patent application number DE 102020213305.0 filed Oct. 21, 2020 and to European patent application number EP21193309.8 filed Aug. 26, 2021, the entire contents of each of which are hereby incorporated herein by reference.

FIELD

Example embodiments of the invention generally relate to a method for use in generating a computer-based visualization of 3D medical image data.

BACKGROUND

Computer-based visualizations of datasets representing a volume may be generated using techniques generally known as volume rendering. Such datasets may be referred to as volumetric datasets. Volume rendering may, for example, be used to visualize a volumetric dataset produced by a medical imaging process, such as a CT scanning process or the like. In the field of medicine, volume rendering may allow for a radiologist, a surgeon or a therapist to visualize and thereby understand and interpret data representing anatomy. Providing a visualization of such data may, for example, be used for diagnosis, teaching, patient communication etc.

Typically, volume rendering techniques involve applying a visual parameter mapping to image data forming the volumetric dataset being rendered, for example by way of a classification of the image data by the application of a transfer function. This mapping provides for one or more visual parameters to be assigned to the image data. The assigned visual parameters can then be used to generate a visualization of the volumetric dataset. For example, the volumetric dataset may comprise a plurality of voxels and a mapping process may be performed to assign to each of the voxels visual parameter data, such as an opacity and a color. The visual parameters assigned by the mapping process can then be used in a volume rendering technique, to generate a visualization of the volume. For example, an integration-based direct volume rendering technique may be performed in which one or more sample rays are cast through the volume for each pixel in the visualization to be generated. In such a technique, each ray may be sampled at a plurality of points to compute an integral based on the visual parameter data and the result of the integral may be used to determine a color value for the corresponding pixel.

SUMMARY

According to a first embodiment of the present invention, there is provided a method for use in generating a computer-based visualization of 3D medical image data, the method comprising:
receiving 3D medical image data;
performing a selection process to select first image data forming a first portion of the 3D medical image data, the first image data representing a first anatomical object of a given type;
performing an analysis process on the first image data, wherein a parameter of the analysis process is based on the given type of the first anatomical object; and
determining, based at least in part on a result of the analysis process, a visual parameter mapping for the first portion for use in a rendering process for generating a visualization of the 3D medical image data.

According to a second embodiment of the present invention, there is provided a method of generating a computer-based visualization of 3D medical image data, the method comprising:
performing a method according to the first embodiment to obtain a visual parameter mapping for a first portion of 3D medical image data; and
performing a rendering process for generating a visualization of the 3D medical image data, wherein performing the rendering process comprises applying the visual parameter mapping for the first portion of the 3D medical image data.

According to a third embodiment of the present invention, there is provided a set of machine-readable instructions which when executed by a processor cause a method according to the first embodiment or the second embodiment to be performed.

According to a fourth embodiment of the present invention, there is provided a machine-readable medium comprising a set of machine-readable instructions according to the third embodiment.

According to a fifth embodiment of the present invention, there is provided apparatus comprising:
a processor; and
a storage comprising a set of machine-readable instructions which when executed by the processor cause the processor to perform a method according to the first embodiment or the second embodiment.

According to another embodiment, a computer-implemented method for providing a visualization object is provided. In this case, the visualization object visualizes a three-dimensional anatomical region of a patient, which is represented by medical volume data (or 3D medical image data), for a user. The method includes:
receiving a selection command of the user, the selection command indicating the patient to be analyzed (or reviewed or diagnosed);
based upon the selection command, calling data assigned to the patient;
determining a medical context information item based upon the assigned data;
selecting suitable volume data of the patient based upon the medical context information item and, optionally, the selection command;
based upon the medical context information item, identifying one or more (anatomical) structures in the selected volume data;
determining a mapping rule for mapping the volume data on a visualization object for the user, wherein the mapping rule is determined taking account of the medical context information item and/or the identified structures;
calculating the visualization object based upon the mapping rule;
providing the visualization object for the user.

According to a further embodiment, a system for providing a visualization object is disclosed. The visualization object represents a three-dimensional anatomy of a patient, which is represented by medical volume data, for a user. The system comprises:

an interface for receiving a selection command of the user, the selection command indicating the patient to be analyzed, and for receiving medical volume data; and a computing unit which is embodied:

to call/retrieve based upon the selection command data assigned to the patient;

to determine based upon the assigned data a medical context information item;

to select based upon the medical context information item and, optionally, the selection command, suitable volume data of the patient;

to identify based upon the medical context information item one or more organs in the selected volume data;

to determine based upon the medical context information item and/or the identified organs a mapping rule for mapping the volume data on a visualization object for a user;

to calculate the visualization object based upon the mapping rule; and to provide the visualization object for the user.

In a further embodiment, the invention relates to a computer program product which comprises a program and which is directly loadable into a memory of a programmable computing unit and which has program means, e.g., libraries and auxiliary functions, for carrying out a method for visualizing a three-dimensional object, in particular in accordance with the aforementioned embodiment, when the computer program product is executed.

Further, the invention relates in a further embodiment to a computer program product which comprises a program and which is directly loadable into a memory of a programmable computing unit and which has program means, e.g., libraries and auxiliary functions, for carrying out a method for providing a trained function, in particular in accordance with the aforementioned embodiment, when the computer program product is executed.

Further, the invention relates in a further embodiment to a method for use in generating a computer-based visualization of 3D medical image data, the method comprising:

receiving 3D medical image data;

performing a selection process to select first image data forming a first portion of the 3D medical image data, the first image data representing a first anatomical object of a type;

performing an analysis process on the first image data, a parameter of the analysis process being based on the type of the first anatomical object; and determining, based at least in part on a result of the analysis process performed, a visual parameter mapping for the first portion for use in a rendering process for generating the computer-based visualization of the 3D medical image data.

Further, the invention relates in a further embodiment to a method of generating a computer-based visualization of 3D medical image data, the method comprising:

performing the method of an embodiment to obtain a visual parameter mapping for a first portion of 3D medical image data; and performing a rendering process for generating the computer-based visualization of the 3D medical image data, wherein the performing of the rendering process includes applying the visual parameter mapping for the first portion of the 3D medical image data.

Further, the invention relates in a further embodiment to a non-transitory machine-readable medium storing a set of machine-readable instructions which, when executed by at least one processor, configure the at least one processor to perform the method of an embodiment.

Further, the invention relates in a further embodiment to an apparatus, comprising:

a processor; and a storage storing a set of machine-readable instructions which, when executed by the processor, cause the processor to perform at least:

receiving 3D medical image data;

performing a selection process to select first image data forming a first portion of the 3D medical image data, the first image data representing a first anatomical object of a type;

performing an analysis process on the first image data, a parameter of the analysis process being based on the type of the first anatomical object; and determining, based at least in part on a result of the analysis process performed, a visual parameter mapping for the first portion for use in a rendering process for generating a computer-based visualization of the 3D medical image data.

BRIEF DESCRIPTION OF THE DRAWINGS

The present invention will now be described, by way of example only, with reference to the following figures, in which.

DETAILED DESCRIPTION OF THE EXAMPLE EMBODIMENTS

Figure 1:
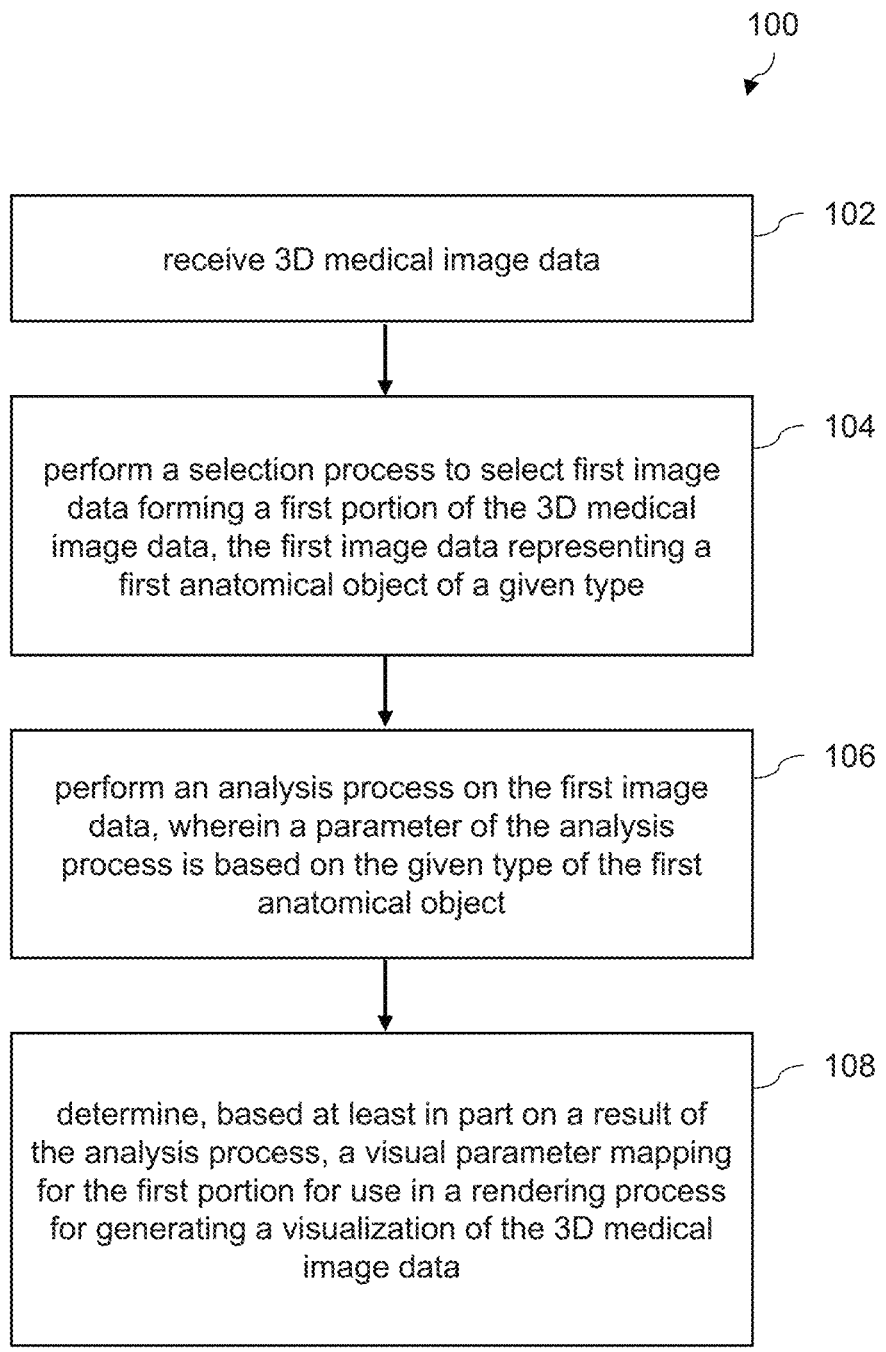
FIG. 1 shows a flowchart representation of a method for use in generating a computer-based visualization of 3D medical image data according to the present disclosure.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules.

Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the present invention, there is provided a method for use in generating a computer-based visualization of 3D medical image data, the method comprising:
  receiving 3D medical image data;
  performing a selection process to select first image data forming a first portion of the 3D medical image data, the first image data representing a first anatomical object of a given type;
  performing an analysis process on the first image data, wherein a parameter of the analysis process is based on the given type of the first anatomical object; and
  determining, based at least in part on a result of the analysis process, a visual parameter mapping for the first portion for use in a rendering process for generating a visualization of the 3D medical image data.

The analysis process may comprise determining one or more characteristics of the first image data. The one or more characteristics of the first image data may be determined based on the parameter of the analysis process.

The one or more characteristics of the first image data may comprise one or more characteristics of a distribution of first voxel values of the first image data, and the analysis process may comprise analyzing the distribution of the first voxel values to determine the one or more characteristics of the distribution.

The one or more characteristics of the distribution may comprise a voxel value or a range of voxel values which satisfy a pre-determined criterion.

The pre-determined criterion may define a voxel value or a range of voxel values associated with a local or global maximum in the distribution.

Determining the visual parameter mapping may comprise, based on the result of the analysis process, determining a function which defines the visual parameter mapping.

The method may comprise determining, based on the given type of the first anatomical object, the parameter of the analysis process.

A parameter of the selection process may be based on the given type of the first anatomical object represented by the first image data.

A or the parameter of the selection process may be determined based on contextual information relating to the 3D medical image data.

A or the parameter of the analysis process may be determined based on contextual information relating to the 3D medical image data.

The contextual information relating to the 3D medical image data may, for example, be one or more of: textual information identifying a medical context of the 3D medical image data; medical history information associated with the 3D medical image data.

The visual parameter mapping may be a transfer function for use in a volume rendering process.

The transfer function may be configured to provide opacity and/or color values for the first image data for use in the volume rendering process.

The first anatomical object may comprise an anatomical organ.

The 3D medical image data may comprise a plurality of 3D medical image datasets, and the selection process may comprise: selecting a first 3D medical image dataset of the plurality of 3D medical image datasets; identifying a portion of the first 3D medical image dataset representing the first anatomical object; selecting a second 3D medical image dataset of the plurality of 3D medical image datasets; and selecting, based on the identified portion of the first 3D medical image dataset, the first image data from the second 3D medical image dataset.

According to a second embodiment of the present invention, there is provided a method of generating a computer-based visualization of 3D medical image data, the method comprising:
  performing a method according to the first embodiment to obtain a visual parameter mapping for a first portion of 3D medical image data; and
  performing a rendering process for generating a visualization of the 3D medical image data, wherein performing the rendering process comprises applying the visual parameter mapping for the first portion of the 3D medical image data.

According to a third embodiment of the present invention, there is provided a set of machine-readable instructions which when executed by a processor cause a method according to the first embodiment or the second embodiment to be performed.

According to a fourth embodiment of the present invention, there is provided a machine-readable medium comprising a set of machine-readable instructions according to the third embodiment.

According to a fifth embodiment of the present invention, there is provided apparatus comprising:
- a processor; and
- a storage comprising a set of machine-readable instructions which when executed by the processor cause the processor to perform a method according to the first embodiment or the second embodiment.

According to another embodiment, a computer-implemented method for providing a visualization object is provided. In this case, the visualization object visualizes a three-dimensional anatomical region of a patient, which is represented by medical volume data (or 3D medical image data), for a user. The method includes:
- receiving a selection command of the user, the selection command indicating the patient to be analyzed (or reviewed or diagnosed);
- based upon the selection command, calling data assigned to the patient;
- determining a medical context information item based upon the assigned data;
- selecting suitable volume data of the patient based upon the medical context information item and, optionally, the selection command;
- based upon the medical context information item, identifying one or more (anatomical) structures in the selected volume data;
- determining a mapping rule for mapping the volume data on a visualization object for the user, wherein the mapping rule is determined taking account of the medical context information item and/or the identified structures;
- calculating the visualization object based upon the mapping rule;
- providing the visualization object for the user.

Expressed differently, a visualization of the volume data adapted to the conditions of the respective individual case is automatically generated when a patient case is called. In particular, relevant (anatomical) structures can be visualized in a targeted fashion by way of a suitable mapping rule. This enables individual representation of individual structures. At the same time, the adjustments and adaptations to be undertaken by the user are reduced, further increasing the usability.

Thus, computer-implemented methods and apparatuses for providing a visualization object are provided, the visualization object being suitable for visualizing a three-dimensional anatomical region of a patient, which is represented by volume data, for a user. In the process, medical context information items (or contextual information) are derived for the respective case, facilitating an automated and targeted definition of a suitable visualization object. In particular, based upon the context information items one or more structures to be visualized are identified in the selected volume data, which structures, based upon the context data, are particularly relevant to the user. These structures to be visualized can then be automatically taken into account on a separate basis when calculating the visualization object, which may improve the result. In particular, individually adapted visualization parameters can thus be determined for each structure to be visualized, as a result of which the individual structures to be visualized can be reproduced in optimal fashion.

In this context, a structure can be, in particular, an organ, an anatomy, a tissue structure, an implant, a tissue change and the like in the anatomical region of the patient. Expressed differently, an identified structure can be referred to as structure to be represented or structure to be visualized. Another expression for (anatomical structure) may be "anatomical object".

In particular, the user can be the recipient of the visualization (object) and hence the person for whom the visualization was created. In particular, the user can be a physician or the patient.

In particular, a visualization object can comprise a two-dimensional visualization image or a time-resolved sequence of a plurality of individual visualization images.

The volume data can contain a multiplicity of voxels. A voxel ("volume pixel" or three-dimensional pixel) is a volume element which represents a value on a regular grid in three-dimensional space. Voxels are analogous to pixels, which represent two-dimensional image data. Like in the case of pixels, the voxels themselves typically do not contain their position in space (their coordinates) but their coordinates are derived based upon their positions relative to other voxels (i.e., their positions in the data structure forming a single volume image). The value of a voxel can represent different physical properties of the three-dimensional object, such as, e.g., a local density. In computed tomography recordings (CT scans), the values are expressed for example in Hounsfield units, which represent the opacity of an imaged material in relation to x-rays. Hence, the volume data describe a three-dimensional anatomical region in a patient volume. In particular, the volume data can specify a density (in particular an inhomogeneous density) of the anatomical region. Another expression for volume data may be 3D medical image data.

In particular, the volume data can be provided by a medical imaging method. The imaging methods can be based on fluoroscopy, computed tomography (CT), magnetic resonance imaging (MRI), ultrasound and/or positron emission tomography (PET), for example. Accordingly, the three-dimensional object can be a body or body part of a patient. In this case, the three-dimensional object can comprise one or more organs of the patient.

Further, the volume data can be four-dimensional data, with three spatial and one temporal dimension. Further, the volume data can comprise a plurality of individual volume data records, each of which, in particular, may have been generated by different imaging modalities.

In this case, mapping the volume data by way of the mapping rule can be implemented by way of an image synthesis algorithm. In particular, the image synthesis algorithm can be considered to be a computer program product which is embodied to map the volume data on a two-dimensional projection surface or to render the volume of the three-dimensional body or to perform volume rendering of the three-dimensional body. In this case, the projection surface is given by the visualization image. The image synthesis algorithm can have program constituents in the form of one or more instructions for a processor for calculating the visualization image. The visualization image is composed of a plurality of visualization pixels. The resolution of the visualization image in relation to the visualization pixels can be spatially constant or uniform or spatially uniform, in particular. By way of example, other terms for the image synthesis algorithm include "renderer", "rendering algorithm" or "volume renderer". By way of example, the image synthesis algorithm can be provided by virtue of being kept available in a memory device or being loaded into a main memory of a suitable data processing device or being provided for application in general terms.

Here, the image synthesis algorithm can implement various methods for visualizing a volume data record, either individually or in combination. By way of example, the image synthesis algorithm can comprise a ray casting module and/or a path tracing module.

By way of example, the provision of the volume data can comprise keeping available and/or calling the volume data in and from a memory device (such as a database), respectively, and/or loading of the volume data, for example into a main memory of a suitable data processing device, or general making available for an application or use.

By way of example, the provision of the assigned data can comprise keeping available and/or calling the context data in and from a memory device (such as a database), respectively, or loading of the assigned data, for example into a main memory of a suitable data processing device, or general making available for an application or use. In particular, the assigned data differ from the volume data. The assigned data can relate to information items relevant to the visualization. By way of example, they can indicate which perspectives, transfer functions or which partial objects of the object to be visualized are particularly relevant to the visualization. In particular, the assigned data may contain natural speech. By way of example, the structure particularly relevant to the visualization can be disclosed in words in the assigned data. By way of example, if a medical report (as a form of assigned data) contains explanations relating to the liver of the patient, it is possible to deduce that this organ should be predominantly displayed in the visualization. In particular, the assigned data may comprise non-image data.

In particular, the assigned data can be assigned to the volume data record by virtue of being linked to the same patient. By way of example, the assigned data may comprise one or more medical reports, physician's letters, records of consultations with other users or patients, medical histories, laboratory data and/or demographic information items about the patient. The assigned data can be available, for example, in the form of an electronic patient record and can be stored in an appropriate information system (for instance: a hospital information system). Additionally, the assigned data may comprise generically relevant information items for the patient, for instance one or more guidelines and/or one or more electronic textbooks or compendia. Further, the assigned data may relate to the user and, for example, indicate one or more user preferences.

In particular, the mapping rule can be understood to be an instruction of how the volume data can be suitably visualized against the background of the clinical context information item. Another expression for mapping rule can be "visual parameter mapping". Returning to the aforementioned example, a dedicated viewing angle, a dedicated scene lighting, and a dedicated color scheme for imaging the volume data can be chosen for a visualization of the liver. Moreover, less relevant regions of the volume data in the visualization can be omitted or cut away or represented transparently. The mapping rule can comprise representation parameters (or visual parameters or transfer parameters). Representation parameters are often very complex. They assign a certain color, transparency, contrast, lighting, sharpness and the like to each grayscale value in the three-dimensional volume. In general terms, the representation parameters influence the type of representation of objects of the corresponding object type in the visualization image output to the user. Expressed differently, a mapping rule can comprise one or more transfer functions.

In particular, the medical context information item (or the contextual information) can be a medical question which a user must address in a patient's case. Moreover, the context information item can comprise an indication of a medical diagnosis, a demographic information item in respect of the patient, a next step in a medical guideline and the like.

According to some examples, the identification is implemented based upon a segmentation of the volume data, the segmentation preferably being implemented based upon the clinical context information item.

The segmentation allows relevant structures to be selected, wherein the relevance can be weighted by the context information item. In particular, a shape segmentation can be used within the scope of the segmentation. By way of example, use can be made of segmentation masks in order to identify structures such as the lungs of the patient in the volume data. All or only some of the segmented structures can be identified as structure to be represented. Preferably, a dynamic choice can be made from the set of segmented structures based upon the context information item in the identification step.

According to some examples, the mapping rule comprises a partial mapping rule for each identified structure and the determination step further comprises specifically optimizing (or, expressed differently, adapting) the partial mapping rules for each identified structure, wherein the optimization (adaptation) for each partial mapping rule is implemented in particular independently of the respective other partial mapping rules.

By using a plurality of partial mapping rules, it is possible to specifically optimize the visualization for each structure and this can lead to significantly better representation of the individual structures in comparison with a global mapping rule that is identical for all structures. Moreover, this facilitates a simple dynamic adaptation of the visualization object should a modified clinic context information item indicate different structures to be identified. Each partial mapping rule can comprise separate representation parameters which assign a certain color, transparency, contrast, lighting, sharpness and the like to each voxel value. Expressed differently, a partial mapping rule can comprise at least one separate transfer function.

According to some examples, the adaptation/optimization for each identified structure comprises extracting an image information item from the volume data (in particular from the volume data assigned to the respective identified structure) and adapting the partial mapping rule based upon the image information item.

By evaluating the image information item, not only is it possible to adapt the mapping rule to the clinical context, but also to adapt the mapping rule to the respective conditions of the patient and the recording parameters used when recording the volume data—to be precise in selective fashion for each structure since this happens for each partial mapping rule. According to the invention, this makes it possible to take account of the fact that image information items of the structures behave differently from recording to recording and from patient to patient. This facilitates not only a structure-specific adaptation but also a patient-specific or recording-specific adaptation, and hence a multidimensional adaptation, of the mapping rule.

According to some examples, the method further comprises the step of providing one or more recording parameters which describe one or more conditions under which the volume data were generated, wherein the recording parameters are taken into account when adapting the partial mapping rules. By way of example, the recording parameters may comprise a kV specification in the case of a CT recording or an MRI sequence in the case of an MRI recording. Taking the recording parameters into account allows a better adaptation of the partial mapping rules to be implemented.

According to some examples, adapting the partial mapping rules can be implemented as an intensity-based segmentation. Taking account of the image information item allows relevant regions of the structure to be delimited even better from surrounding structures, for example proceeding from a shape-based segmentation, and thus to be worked out well for the visualization.

In one alternative, the volume data of the structure in comparison with the remaining anatomical region or the other identified structures can also be used in addition to the volume data of the respective structure.

According to some examples, the image information item comprises a statistical frequency or distributions of the image values (voxel values) of the volume pixels belonging to the identified structure. By way of example, color values or grayscale values can be evaluated here as image values.

According to some examples, the volume data were at least partly generated using a computed tomography method and the image information item comprises a statistical frequency or distribution of the Hounsfield units (HU).

This facilitates a simple capture of different contributions in CT imaging and, as a consequence thereof, a good adaptation of the partial mapping rules, for example by an additional intensity-based or contrast-based selection of the voxels to be represented.

In MR imaging, the contrast ratios are significantly more variable than in CT. The contrast behavior is set by way of the MR sequence and the measurement protocol. An anatomical segmentation must take account of, model, or be robust against this variability. Naturally, the anatomical shape features of organs or structures are also present in MR imaging. A segmentation based purely on shape recognition is directly employable in the field of MRI. If the intensity characteristic should also be taken into account, this requires a suitable parameterization of the segmentation. According to embodiments, the parameterization can be implemented by way of:
  prior knowledge about the MR imaging;
  a mathematical-physical derivation from the properties of the tissue taking account of the field strength, sequence and protocol and, in a simple case, with the aid of the Bloch equations; and/or
  available reference images/databases.

In a further case, such a segmentation can also be carried out with the aid of so-called MR fingerprinting methods, which intrinsically contain multi-contrast behavior in the imaging sequence itself.

According to some examples, the adaptation for each identified structure further comprises determining at least two image information contributions in the image information item and adapting the partial mapping rule based upon the image information contributions.

By way of example, the image information contributions can be brought about by "fitting" one or more characteristic functions to the image information item (such as a distribution of voxel values). The image information contributions can originate from different tissue types, such as, e.g., bone or soft tissue. By determining the image information contributions, the partial mapping rules can be optimized in an even more targeted fashion.

According to some examples, the adaptation for each identified organ/structure further comprises a comparison of the image information item with a reference image information item and an adaptation of the partial mapping rule based upon the comparison.

The reference image information item can be associated with a partial mapping rule that is optimal to this end. By way of the comparison, it is possible to find deviations between the image information item and the reference image information item, which in turn may indicate a possible adaptation of the optimal partial mapping rule for the available volume data.

According to some examples, determining the mapping rule further comprises a selection of one or more partial mapping rules from a pool of partial mapping rules based upon the identified structures and/or the assigned data.

According to some examples, adapting the partial mapping rule for the structure to be displayed in each case comprises a selection of a preset partial mapping rule assigned to the respective structure to be displayed and an adaptation of the preset partial mapping rule in order to create the adapted partial mapping rule.

As a result, it is already possible to find a good starting point for the adaptation of the partial mapping rules.

According to some examples, the partial mapping rules are adapted in each case with the clinical context information item and/or the associated data being taken into account, as a result of which a targeted adaptation of the partial mapping rules is ensured.

According to some examples, the adaptation of the partial mapping rules is implemented by the application of a trained function that is embodied to specifically provide a partial mapping rule for each identified organ, in particular based upon the clinical context information item and/or the assigned data.

In general, a trained function maps input data on output data. In this case, the output data can furthermore depend on one or more parameters of the trained function, in particular. The one or more parameters of the trained function can be determined and/or adapted by training. Determining and/or adapting the one parameter or the plurality of parameters of the trained function can be based, in particular, on a pair of training input data and associated training output data, wherein the trained function is applied to the training input data to generate training imaging data. In particular, the determination and/or adaptation can be based on a comparison of the training imaging data and the training output data. In general, a trainable function, i.e., a function with parameters that have not yet been adapted, is also referred to as a trained function.

Other terms for trained function include trained mapping rule, mapping rule with trained parameters, function with trained parameters, algorithm based on artificial intelligence, and machine learning algorithm. An artificial neural network is an example of a trained function. Instead of the term "artificial neural network", the term "neural network" can also be used. In principle, a neural network is constructed like a biological neural network, for instance a human brain. In particular, an artificial neural network comprises an input layer and an output layer. It can further comprise a plurality of layers between input layer and output layer. Each layer comprises at least one node, preferably a plurality of nodes. Each node can be understood to be a biological processing unit, for example a neuron. Expressed differently, each neuron corresponds to an operation that is applied to input data. Notes of one layer can be connected by edges or connections to nodes of other layers, in particular by directed edges or connections. These edges or connections define the data flow between the nodes of the network. The edges or connections are associated with a parameter which is frequently referred to as "weight" or "edge weight". This parameter can regulate the importance of the output of a first node for the input of a second node, with the first node and the second node being connected by an edge.

In particular, a neural network can be trained. In particular, the training of a neural network is carried out based upon the training input data and the associated training output data in accordance with a "supervised" learning technique ("supervised learning" is the specialist term), wherein the known training input data are entered into the neural network and the output data generated by the network are compared to the associated training output data. The artificial neural network learns and independently adapts the edge weights for the individual nodes for as long as the output data of the last network layer do not sufficiently correspond to the training output data.

In particular, a trained function can also be a deep artificial neural network ("deep neural network" and "deep artificial neural network" are specialist terms).

According to some examples, the calculation is implemented using a volume rendering algorithm which, in particular, implements a method based on ray casting and/or path tracing and the mapping rule has one or more transfer functions.

Such methods allow particularly realistic visualizations to be generated, increasing the usefulness of the method. The specified methods are complicated in application. However, by taking into account according to the invention the context data, the specified methods can be operated easily and automatically supply a visualization that is as optimal as possible.

According to some examples, the mapping rule is embodied such that the identified organs are emphasized for the user in the visualization object. In particular, this can be brought about by virtue of not visualizing other image constituent parts of the volume data.

According to some examples, the mapping rule has a global mapping rule, the global mapping rule defining one or more overarching scene properties of the visualization image. By way of example, these scene properties can relate to a perspective, a magnification or a scene lighting, which apply uniformly to all identified structures, as a result of which a uniform image impression arises despite the emphasis on individual structures.

According to some examples, the mapping rule is embodied in such a way that the visualization object comprises a time-resolved sequence of a plurality of individual images. In this case, at least two of the individual images may represent a different perspective of the volume data record.

As a result, it is possible to offer, e.g., video material to the user as well, as a result of which temporal or geometric relationships become more easily comprehensible (the latter in particular when using different perspectives in the individual images).

According to some examples, the method further includes a step of receiving a user input in respect of the clinical context information item, wherein the clinical context information item is additionally determined based upon the user input.

According to some examples, the user input may include a voice input by a user, which can be evaluated by a computer linguistics algorithm. By way of example, this can achieve a simple voice control of the method.

According to some examples, the selected volume data comprise a first volume data record which was recorded by a first imaging modality and comprise a second volume data record which was recorded by a second imaging modality that differs from the first. The method then further comprises a registration of the first volume data record with the second volume data record, wherein the step of determining the mapping rule is further additionally implemented based upon the registration.

The registration can be implemented by bearing the patient or by way of an image-data-based registration. Now, a broader parameter space of intensities is available for the identification/the segmentation. In this multi-dimensional intensity space, the organs themselves have a greater distance than in the sole observation of one modality. This greater distance can be used to improve and stabilize the identification/segmentation. In part, a case-specific parameterization can be used to this end (as explained above for example in conjunction with MR data).

Then, the registered multi-dimensional intensity space can be used together with a multi-dimensional partial mapping rule (transfer function). Hence, the specific contribution of a voxel to the overall image can be implemented from only one modality or from any combination. The automatic/partly automatic optimization of the partial mapping rule in respect of the structures to be visualized in the intensity space is optionally advantageous.

According to some examples, the method further includes the step of providing volume data for the patient, wherein suitable volume data are selected from the volume data provided.

It is also possible to provide the volume data for example by way of suitable access to an appropriate archiving system, for instance a PACS system. By the selection of volume data relevant to the medical question, it is possible to automatically ascertain suitable initial data, further unburdening the user.

According to a further embodiment, a system for providing a visualization object is disclosed. The visualization object represents a three-dimensional anatomy of a patient, which is represented by medical volume data, for a user. The system comprises:
  an interface for receiving a selection command of the user, the selection command indicating the patient to be analyzed, and for receiving medical volume data; and
  a computing unit which is embodied:
    to call/retrieve based upon the selection command data assigned to the patient;
    to determine based upon the assigned data a medical context information item;
    to select based upon the medical context information item and, optionally, the selection command, suitable volume data of the patient;
    to identify based upon the medical context information item one or more organs in the selected volume data;
    to determine based upon the medical context information item and/or the identified organs a mapping rule for mapping the volume data on a visualization object for a user;
    to calculate the visualization object based upon the mapping rule; and
    to provide the visualization object for the user.

The computing unit can be embodied as a centralized or decentralized computing unit. The computing unit can comprise one or more processors. The processors can be embodied as a central processing unit (CPU) and/or as a graphics processing unit (GPU). The computing unit can be embodied as a so-called system-on-a-chip (SoP), which controls all functions of a device. Alternatively, the computing unit can be implemented as a local or cloud-based processing server.

In general, the interface can be embodied for data exchange between the computing device and further components. The interface can be implemented in the form of one or more individual data interfaces which may comprise a hardware and/or software interface, for example a PCI bus, a USB interface, a FireWire interface, a ZigBee interface or a Bluetooth interface. The interface can further comprise an interface of a communications network, wherein the communications network can have a local area network (LAN), for example an intranet, or a wide area network (WAN). Accordingly, the one or more data interfaces may comprise a LAN interface or a wireless LAN interface (WLAN or Wi-Fi).

The advantages of the proposed apparatus substantially correspond to the advantages of the proposed method. Features, advantages or alternative embodiments can likewise be transferred to the other claimed subjects, and vice versa.

In a further embodiment, the invention relates to a computer program product which comprises a program and which is directly loadable into a memory of a programmable computing unit and which has program means, e.g., libraries and auxiliary functions, for carrying out a method for visualizing a three-dimensional object, in particular in accordance with the aforementioned embodiment, when the computer program product is executed.

Further, the invention relates in a further embodiment to a computer program product which comprises a program and which is directly loadable into a memory of a programmable computing unit and which has program means, e.g., libraries and auxiliary functions, for carrying out a method for providing a trained function, in particular in accordance with the aforementioned embodiment, when the computer program product is executed.

Here, the computer program products may comprise software with a source code, which still needs to be compiled and bound or only interpreted, or an executable software code which only still needs to be loaded into the processing unit for execution purposes. As a result of the computer program products, the methods can be carried out quickly, in identically repeatable fashion and in robust fashion. The computer program products are configured in such a way that they can carry out the method steps according to the invention via the computing unit. Here, the computing unit must satisfy the requirements in each case, for example have an appropriate main memory, an appropriate processor, an appropriate graphics card or an appropriate logic unit, so that the respective method steps can be carried out efficiently.

By way of example, the computer program products are stored on a computer-readable storage medium or saved on a network or server, from where they can be loaded into the processor of the respective computing unit, which may be directly connected to the computing unit or be embodied as part of the computing unit. Furthermore, control information items of the computer program products may be stored on a computer-readable storage medium. The control information items of the computer-readable storage medium may be embodied in such a way that they carry out a method according to the invention when the data medium is used in a computing unit. Examples of computer-readable storage media include a DVD, a magnetic tape or a USB stick, on which electronically readable control information items, in particular software, are stored. If these control information items are read from the data medium and stored in a computing unit, it is possible to carry out all embodiments according to the invention of the methods described above. Thus, the invention can also proceed from the computer-readable medium and/or from the computer-readable storage medium. The advantages of the proposed computer program products or of the associated computer-readable media substantially correspond to the advantages of the proposed methods.

Modeling, reconstructing or visualizing three-dimensional objects has a broad field of application in the fields of medicine (e.g., CT, PET), physics (e.g., electron structure of large molecules) or geophysics (condition and relative position of layers of the earth). Typically, the object to be examined is irradiated (e.g., via electromagnetic waves or acoustic waves) in order to examine the condition thereof. The scattered radiation is detected and properties of the body are ascertained from the detected values. Usually, the result consists in a physical variable (e.g., density, tissue type, elasticity, velocity), the value of which is ascertained for the body. As a rule, use is made here of a virtual grid, at the grid points of which the value of the variable is ascertained. These grid points are usually referred to as voxels. The term "voxel" is a portmanteau formed from the terms "volume" and "pixel". A voxel corresponds to the spatial coordinate of a grid point, which is assigned the value of a variable at this location. Here, this is usually a physical variable that can be represented as a scalar or vector field, i.e., the corresponding field value is assigned to the spatial coordinate. By interpolating the voxels, it is possible to obtain the value of the variable or of the field at any object points (i.e., at any location points of the object examined).

To visualize the volume data, a three-dimensional representation of the examined object or body is generated from the voxels on a two-dimensional representation surface (e.g., a screen or a panel or lens of so-called "augmented reality glasses"). Expressed differently, voxels (defined in three dimensions) are mapped on pixels (defined in two dimensions) of a two-dimensional visualization image. The pixels of the visualization image are also referred to as visualization pixels below. The mapping is usually referred to as a volume rendering. How information items contained in the voxels are reproduced via the pixels depends on how the volume rendering is carried out.

One of the most frequently used methods for volume rendering is so-called ray casting (cf. Levoy: "Display of Surfaces from Volume Data", IEEE Computer Graphics and Applications, issue 8, no. 3, May 1988, pages 29-37, the entire contents of which are hereby incorporated herein by reference). In ray casting, simulated rays emanating from the eye of an imaginary observer are transmitted through the examined body or the examined object. Along the rays, RGBA values are determined for sampling points from the voxels and combined to form pixels for a two-dimensional image by way of alpha compositing or alpha blending. Here, the letters R, G and B in the expression RGBA represent the color components red, green and blue, from which the color contribution of the corresponding sampling point is composed. A represents the ALPHA value, which represents a measure for the transparency at the sampling point. The respective transparency is used in the superposition of RGB values at sampling points to form the pixel. Lighting effects are usually taken into account by way of a lighting model within the scope of a method referred to as "shading".

A further method for volume rendering is the so-called path tracing method (cf. Kajiya: "The rendering equation", ACM SIGGRAPH Computer Graphics, issue 20, no. 4, August 1986, pages 143-150, the entire contents of which are hereby incorporated herein by reference). Here, a plurality of simulated rays are shot into the volume data per visualization pixel, the simulated rays then interacting with the volume, i.e., are reflected, refracted or absorbed, wherein at least one random ray is generated every time (except in the case of absorption). Each simulated ray thus finds its path through the volume data. The more virtual rays are used per visualization pixel, the more the ideal image is honed in on. Here, use can be made in particular of the processes and methods described in EP 3 178 068 B1, the entire contents of which are hereby incorporated herein in full, by reference.

Users, especially in the medical and clinical field, can be effectively assisted by such visualization methods since such representation provides a quick overview of complex anatomical relationships. By way of example, this allows better planning of surgical interventions. Further, such visualization images facilitate the creation of meaningful medical reports.

A primary technical obstacle in the implementation of a system for interactive volume rendering lies in the targeted adaptation of the representation to the respective requirements when establishing a diagnosis for a specific patient for the purposes of answering a specific clinical problem. Conventional systems are able to generate representations which can optimally reproduce, in full, an anatomical region of the patient which is represented by volume data. However, such global settings are often less suitable for the observation of individual structures as they often cannot sufficiently reproduce the details. In this context, individual structures can be for example organs, implants, bones, vessels, spatial requirements or pathological tissue changes such as for instance tumors. By way of example, if proceeding from a rendered overall representation individual structures should be removed in order to be able to better assess tissue situated therebehind, representation errors sometimes arise to the extent of too much or too little information being removed. This renders corrections necessary, for which the users often have neither the time nor the background knowledge. As a result, there is a reduced acceptance of volume rendering algorithms for clinical diagnoses despite the potential inherent to this technology. In the worst-case scenario, inexpediently chosen global visualization parameters can hide pathologically relevant circumstances and can lead to incorrect decisions.

At least one embodiment of the present invention thus provides an improved method and/or apparatus in this respect, for visualizing volume data. In particular, the problem intended to be addressed in the process is that of providing a visualization method that allows the volume data to be processed in such a way that the visualization thereof is better adaptable to the underlying medical question.

FIG. 1 illustrates a flowchart representation of an example method 100 for use in generating a computer-based visualization of 3D medical image data.

Figure 2:
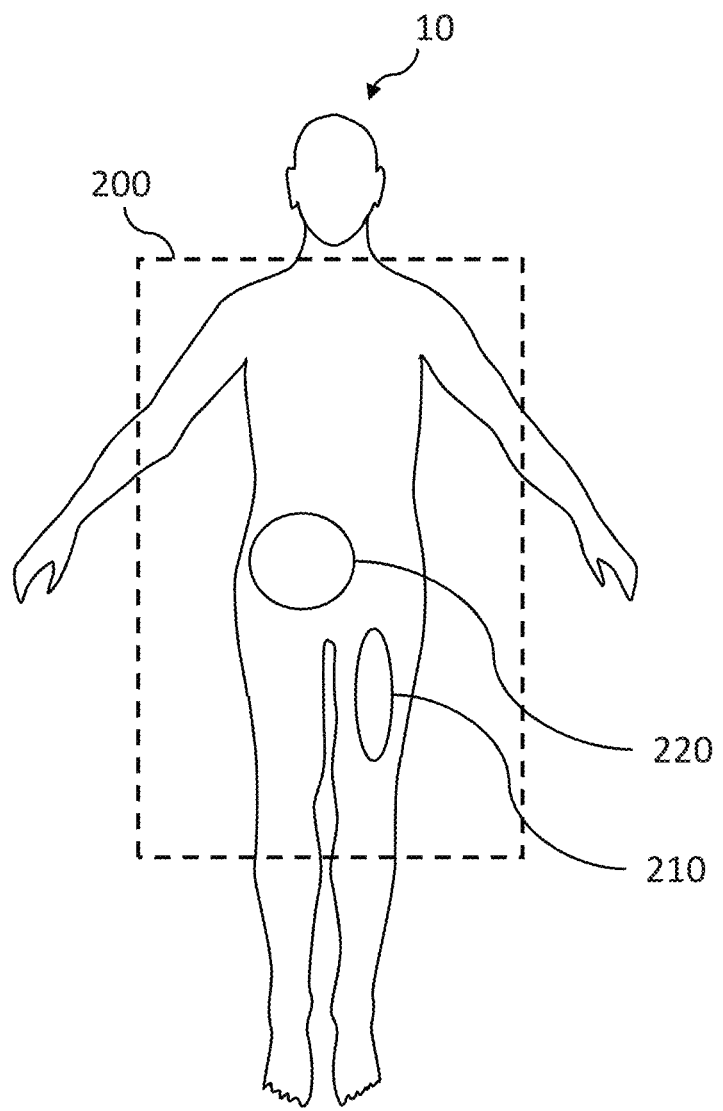
FIG. 2 shows a schematic illustration of an example volume for which 3D medical image data is obtained, the volume comprising example anatomical objects within an anatomy of a patient.

The method 100 comprises, at block 102, receiving 3D medical image data. The 3D medical image data may be received by loading from a memory, sensors, and/or other sources. In general, any scanning modality may be used to produce the 3D medical image data. For example, the scanning modality may comprise the use of computed tomography (CT), or of magnetic resonance imaging (MRI). In some examples a scanning modality comprising the use of positron emission tomography (PET), single photon emission computed tomography (SPECT), ultrasound, or another scan modality may be used. The 3D medical image data may represent an imaged volume within a human or animal anatomy. Turning briefly to FIG. 2, there is illustrated schematically an example of an imaged volume 200 of an anatomy of a patient 10.

The 3D medical image data may have been acquired using a three-dimensional acquisition process, so that it is inherently in a 3D format. As an alternative, the 3D medical image data may have been derived from a set of two-dimensional (2D) images in one or more imaging planes, with each of the 2D images being made up of a plurality of pixels. The 3D medical image data, in some examples, may comprise volumetric data which has been smoothed through interpolation or the like. In another example, an interpolation process could be performed as part of a process of rendering the image data.

In examples, the 3D medical image data comprises a plurality of data elements, also referred to as voxels, each of which includes a value for a measured variable, also referred to as a voxel value. Each voxel corresponds to a one of a plurality of locations that are distributed over the imaged volume 200. Typically, the measured variable corresponds with the type of imaging apparatus used to generate the medical image data. For example, with 3D medical image data generated using an X-ray imaging apparatus, the measured variable may relate to radiodensity, for example the measured variable may be attenuation, e.g. measured on the Hounsfield scale. As another example, with medical image data generated using an MRI apparatus, the measured variable may be a relaxation time of protons in the imaging volume, such as the T1 time constant or the T2 time constant. In some cases, each data element within the 3D medical image data may define the value of the measured variable and the associated location. In other example, the location in the volume 200 to which each data element corresponds is inherent in the structure of the 3D image data, e.g. in the ordering of the data elements. Furthermore, in some cases the 3D medical image data may define, for each location, respective values for two or more measured variables. For example, with 3D medical image data generated using an MRI apparatus, the value of both the T1 time constant and the T2 time constant may be stored for each location.

At block 104, the method comprises performing a selection process to select first image data forming a first portion of the 3D medical image data, the first image data representing a first anatomical object of a given type.

Returning briefly to FIG. 2, there is illustrated schematically an example of a first anatomical object 210 within the image volume 200 of an anatomy of a patient 10. In this example the first anatomical object 210 is a bone of the patient 10. In this example the bone is the femur of the patient.

The selection process of block 104 may be configured to identify, within the 3D medical image data, a sub-set of the 3D medical image data which is determined to represent the anatomical object of the given type. This sub-set of the 3D medical image data may accordingly be selected, by the selection process, as the above-mentioned first image data.

The selection process may be applied to the 3D medical image data in order to select regions of the 3D medical image data representing a given anatomical object, for example, an individual organ such as an individual bone or the liver, or a given organ system, for example, the respiratory system or the skeleton. In one example, the selection process is a segmentation process which is configured to identify regions of the 3D medical image data representing a particular organ, or a particular organ system. Other examples of anatomical objects which may be selected by the selection process are the liver; brain; kidney or kidneys; and lung or lungs.

In some examples, the selection process may be configured to select voxels of the image data which can be identified as representing a particular anatomical object due to a characteristic of the voxel values. In some examples, the selection process comprises a segmentation process which may be intensity-based and/or shape-based. For example, according to one example, a shape-based segmentation may initially be performed to segment a given anatomical object and the shape-based segmentation may later be refined by an intensity-based segmentation.

Various parameters of the selection process may be determined according to the particular anatomical feature or anatomical object which the segmentation is intended to select. In some examples, more than one selection process may be performed, each of which may be configured to select a given anatomical object.

In some examples, a parameter of the selection process is based on the given type of the first anatomical object to be selected. The parameter of the selection process may, for example, define a voxel intensity pattern and/or object shape to be used by the selection process to select voxels representing a given anatomical object. For example, the parameter of the selection process may define the selection process as a segmentation process for segmenting a given type of organ, such as bone, or, alternatively, as a segmentation process for segmenting the liver. For example, where the type of the first anatomical object is bone, the parameter may define the characteristic shape and/or intensity pattern which is used by the segmentation process to identify portions of the volume which represent bone and to segment those portions.

In some examples, a parameter of the selection process may be determined based on contextual information relating to the 3D medical image data. For example, the contextual information may be information relating to the clinical use case for 3D medical image data. The parameter of the selection process may, for example, be determinative of the type of anatomical object the selection process is configured to select. The contextual information may, for example, determine a shape and/or intensity pattern which the segmentation process is configured to identify in order to segment voxels representing a given anatomical object.

As a specific example, the contextual information may be indicative that the clinical use case for the 3D medical image data is related to neurology. The contextual information may then be used to determine a parameter for the selection process which causes the selection process to select a portion of the 3D medical image data representing the brain of the patient. In another example, the contextual information may be indicative that the clinical use case relates to the liver and accordingly this contextual information may be used to determine a parameter for the selection process which causes image data representing the liver to be selected.

The contextual information may be derived from textual information associated with the 3D medical image data. For example, the contextual information may be derived from textual information associated with the 3D medical image data which indicates the medical context of the data. For example, where the 3D medical image data is associated with descriptive meta information, as is the case with data encoded as a Digital Imaging and Communications in Medicine (DICOM) dataset, the contextual information may be derived from the descriptive meta information, which may for example be included in a DICOM header of the DICOM dataset. The textual information may, for example, indicate the scanning methodology used to produce the 3D medical image data. The textual information may, additionally or alternatively, indicate the anatomical features which the scan is intended to image and/or may identify a medical condition to which the scan is related.

In another example, the contextual information may be derived from medical history information associated with the 3D medical image data, for example, from medical data records relating to the patient.

Contextual information which may be used in certain examples of the present method may in some cases be obtained via a suitable data mining process. For example, a natural language processing analysis may be applied to textual data of the patient data. For example, in certain examples, a trained neural network may be applied to medical data relating to the 3D medical image data in order to obtain the contextual information.

At block 106, the method comprises performing an analysis process on the first image data, wherein a parameter of the analysis process is based on the given type of the first anatomical object 210.

In some examples, the analysis process comprises determining one or more characteristics of the first image data. In such examples, the parameter of the analysis process may define a characteristic of the first image data to be determined by the analysis process. For example, the parameter of the analysis process may define a characteristic, to be determined by the analysis process, of a distribution of voxel values of the first image data. For example, if the first anatomical object is bone, then the parameter of the analysis process may be a characteristic of the image data which is associated with image data representing bone, such as a peak in the distribution of voxel values of the first image data or a range of voxel values satisfying a given pre-determined criterion. Determining the characteristics of the image data may, for example, comprise determining the voxel values of such peaks and ranges in the distribution. The particular characteristics of the image data which are determined by the analysis process may vary between different types of anatomical object. For example, in the case of bone, the characteristics of the image data which are determined may be different depending on the particular type of the bone. For example, a large bone may be expected to be have more voxel values representing marrow than a small bone and the regions of the distributions of voxel values for large bones and small bones may, accordingly, have different properties. As such, the manner in which the distribution of voxel values may be decomposed into different components may differ between different types of bone and accordingly different characteristics may be determined to characterize the distributions of such different types of bone. In another example, where the anatomical object is the liver, rather than bone, the characteristics determined by the analysis process may be one or more characteristics of the distribution of voxel values which may be associated with respective components of the liver. In yet another example, where a high-density object, such as a metal implant, is expected to be present in the first image data, a characteristic of the first image data which is determined may relate to such a high-density object. For example, a peak in the distribution of the first image data which is related to the high-density object may be determined. In the case of a metal implant, for instance, a peak in the region of approximately 2000 HU may be determined. The voxel value associated with the peak may accordingly be corresponded with the metal implant and used in the determination of the visual parameter mapping to allow the metal implant to be appropriately visualized.

The one or more characteristics of the first image data to be determined by the analysis process may, for example, comprise one or more characteristics of a distribution of first voxel values of the first image data. For example, the analysis process may comprise analyzing the distribution of the first voxel values to determine one or more characteristics of the distribution. In some examples, the distribution of voxel values is represented as a histogram representing the relative frequency with which the voxel values take various particular voxel values or fall into various sub-ranges of voxel values. In such cases, the one or more characteristics of the voxel values may comprise one or more characteristics of the histogram.

The one or more characteristics of the distribution of the first voxel values may comprise a voxel value or a range of voxel values which satisfy a pre-determined criterion. For example, a peak, or mode, in the distribution may be determined. The peak may be a voxel value having the highest frequency in distribution. The peak may be a local or global maximum value in the distribution.

Various other characteristics of the distribution may be determined. For example, a range of voxel values may be determined for which the distribution satisfies a pre-determined criterion. For example, the range of voxel values having non-zero frequencies or frequencies at or above a pre-determined threshold may be determined. Such a range may in some cases be limited to a range of values to one side or another of a given feature in the distribution, such as a peak in the distribution.

As described above, the characteristics of the first image data to be determined in a given example may be dependent on the given type of anatomical object which the first image data represents. For example, the characteristics of the distribution to be determined may be characteristics which are related to anatomical features of the given type of the anatomical object.

In this regard, the inventors have recognised that image data representing a given type of anatomical object tend to have characteristics which are particular to the given type of anatomical object. For example, a distribution of voxel values of image data representing bone tends to have characteristic features which can be associated with different components of the bone. For example, certain specific features of a distribution of voxel values known to represent bone can be associated with the marrow of the bone while other certain specific features can be associated with the cortex of the bone.

The characteristics which are determined by the analysis process may be dependent on the given type of the anatomical object represented by the image data. For example, where the selection process performed at block 104 is configured to select bone, the analysis process may be determined to identify the global peak in the distribution of voxel values as well as respective ranges of non-zero frequency voxel values at voxel values less than and greater than the peak. On the other hand, if the selection process 104 is configured to select image data representing a liver, for example, the analysis process may be configured to determine different characteristics of the image data which are characteristic of image data representing a liver. An example for the case where the first anatomical object is bone will be discussed below in more detail, with reference to FIGS. 3A and 3B.

In some examples, the results of the analysis process obtained at block 106 may be used to refine the selection process performed at block 104. For example, the analysis process may allow voxel values included in the first image data to be identified as not belonging to the first anatomical object, for example, if the voxel values do not fit a typical distribution for the given type of the first anatomical object. Such voxel values may accordingly be ignored when performing the analysis process on the first image data.

In some examples, the method comprises determining the parameter of the analysis process based on the given type of the anatomical object.

Contextual information may in some examples be used to determine a parameter of the analysis process. For example, contextual information may be obtained which is indicative of the type of the first anatomical object. For example, the contextual information may indicate that the first anatomical object is a liver. The contextual information may then be used to determine the form which the analysis process takes. For example, the characteristics of the first image data which are determined by the analysis process may be determined by the type of the first anatomical object, which, in turn, may be indicated by the contextual information. The contextual information may be obtained in any suitable manner, for example, as described above in relation to the selection process.

At block 108, the method 100 comprises, determining, based at least in part on a result of the analysis process, a visual parameter mapping for the first portion, the visual parameter mapping being for applying in a rendering process for generating a visualization of the 3D medical image data.

Using the results of the analysis process, a visual parameter mapping can be determined which is appropriate for visualizing the anatomical object to which the image data relates.

For example, in the example described above where the anatomical object represented by the first image data is bone, the result of the analysis process may include a voxel value corresponding to a peak in the distribution of voxels representing bone. As described above, this voxel value corresponding to the peak and the voxel values greater than the peak having non-zero frequencies may be identified as a voxel value associated with the cortex of the bone. The result of the analysis process may therefore be used to indicate voxel values associated with a particular physical component of the bone, in this example the cortex. Further, in the example where the first anatomical object is bone, as described above, and as will be described in the context of a more detailed example below, the results of the analysis process may be indicative of the voxel values which represent the marrow of the bone, which lie to the left of the peak associated with the cortex of the bone.

Accordingly, based on the result of the analysis process, a visual parameter mapping may be determined for the image data representing the first anatomical object. For example, in the case of bone, since the voxel values representing cortex are known from the analysis process, the visual parameter mapping may be configured to assign to these voxel values a color and an opacity appropriate to be used for visualizing cortex when used in a rendering process. Similarly, since the range of voxel values of the image data representing marrow is known from the analysis process, the visual parameter mapping may be configured to assign to these voxel values a color and an opacity appropriate for visualizing marrow when used in a rendering process. The voxel values corresponding to particular components of an anatomical object, such as cortex or marrow, may vary from patient to patient, for example due to the age of the patient or other factors. By determining characteristics of the first image data and matching those characteristics with particular components of the anatomical object, a visualization of the anatomical object can be provided which is consistent with the given type of the anatomical object.

Determining the visual parameter mapping may involve fitting a function to the distribution of the image data, where the form of the function is determined by the type of object represented by the image data. In some examples, the method may comprise selecting a form of transfer function from a pre-determined pool of forms of transfer functions based on the given type of the anatomical object. The selected form of transfer function may be defined by a number of characteristics which are determined by the type of the anatomical object to which the form of transfer function corresponds. For example, the distribution of voxel values representing an organ of a given type may have characteristic features such as peaks and/or regions of non-zero frequency which are characteristic of the given type of organ. The selected form of transfer function may then be adapted based on the analysis of the first image data to provide a transfer function specifically adapted to the first image data. In some examples, an optimization process may be performed, for example based on a machine learning algorithm, which may, for example, use a neural network, to adapt the given type of transfer function based on the analysis of the first image data. These features can be associated with anatomical features of the organ and used to derive a transfer function which allows these anatomical features to be rendered in an appropriate manner. In this way, a visual parameter mapping can be obtained for a given anatomical object which provides a visualization of that object which is consistent with the type of the anatomical object. For example, a visual parameter mapping can be determined which is configured to provide a consistent representation of bone, in terms of the respective colors and opacities used to represent the marrow and the cortex of the bone. Moreover, the visual parameter mapping can be determined without the need for manual intervention by a user.

The visual parameter mapping determined by the method 100 may then be applied in the rendering process for generating a visualisation of the 3D medical image data.

The visual parameter mapping is configured to be used to assign visual parameter data, such as an opacity and/or a color, to the first image data. The visual parameter mapping may, for example, be a transfer function configured to be applied during a classification process in a direct volume rendering process.

In certain examples, during rendering, the visual parameter mapping obtained by the method 100 is only applied to the first image data forming the portion of the 3D medical image data. That is, image data of the 3D medical image data which is not within the first portion may be assigned visual parameter data in another manner, for example using a different visual parameter mapping. In other examples, image data in the 3D medical image data which is not in the first portion may not be assigned visual parameter data at all, for example, because it is only desired to visualize the anatomical object represented by the first image data. Accordingly, in some examples, the visual parameter mapping for the first image data may be referred to as a partial transfer function, since it provides a transfer function which configured to be used to assign visual parameter data for a given portion of the volume.

Accordingly, examples of the method described above provide for a visual parameter mapping to be determined which is appropriate for visualizing a given anatomical object. By identifying image data representing the anatomical object and analyzing the image data, while taking into account the type of the anatomical object, an appropriate visual parameter mapping for the object can be derived.

The method provides for a visual parameter mapping to be obtained for a portion of the image data representing a given anatomical object which is tailored to the particular object. The method does not rely on applying a fixed mapping for a given type of object wherein, for example, particular voxel values are mapped in a pre-determined manner to a given color and opacity. Rather, the present method allows a visual parameter mapping to be generated which is specifically adapted for visualizing the particular anatomical object represented by the data.

The above-described method also allows for adaptions to a visualization to be computed quickly, for example, in real-time. Furthermore, the method reduces the input required from the user to determine the visual parameter mapping since the visual parameter mapping is generated based on the result of a computerized analysis of the image data. This allows the method to be fast and to not rely on the ability of the user to manually adapt a visual parameter mapping to the particular use case at hand. This is advantageous since a user may typically be unfamiliar with the subtleties of volume rendering and may therefore be neither willing nor capable to adjust the parameters of the rendering process.

The method according to the present disclosure allows for a visual parameter mapping to be determined for each of the anatomical objects which is to be visualized. The different visual parameter mappings can then be applied to produce a visualization of the volume in which each of the objects in the volume is visualized by use of an appropriate specifically adapted visual parameter mapping. Accordingly, rather than providing a single visual parameter to be applied across the entirety of a volumetric dataset, as is the case in certain prior art methods, the approach according to the present disclosure allows a given anatomical object to be visualized using different visual parameter mappings. The visual parameter mapping determined for a given object is specifically adapted based on an analysis of the image data representing the object for visualizing that object and the visual parameter mapping is configured to be applied locally to visualize the object.

The method allows for multiple visual parameter mappings to be obtained for a dataset to corresponding with respective multiple anatomical objects represented in the dataset. These visual parameter mappings may then be applied, e.g. as partial transfer functions, to allow the multiple anatomical objects to be rendered simultaneously, as will be described below in more detail. For example, in some examples, it may be desirable to enable an interactive selection of the anatomical structures which are to be displayed, for example, based on the clinical use case of the volumetric dataset being visualized. For instance, the clinical context of the visualization may be relevant to the liver and therefore require the liver to be displayed in detail, while the lungs may be not as relevant and may thus be shown in less detail or not at all. Further, some clinical use cases may require two or more different objects, e.g. anatomical organs, to be displayed at the same time. In some such examples, the opacity, color, or other visual parameters applied by the visual parameter mappings to the different objects may be determined based on which objects are required to be displayed. For example, if an object which is a focus of the visualization lies behind another object, the other object in the visualization may be made transparent so as not to obstruct the visibility of the object of focus. Additionally, or alternatively, the multiple visual parameter mappings may allow the user to switch between which of the anatomical objects are visualized, while providing an appropriate visualization regardless of which of the anatomical objects is being visualized. Moreover, the method allows for an anatomical object to be selected to be visualized and for a visual parameter mapping for the object to be quickly obtained 'on the fly'. This allows a workflow for the user which is fast and which provides a visualization which is tailored to the use case at hand and which does not require user to be capable of suitably adjusting the rendering parameters.

Figure 3A:
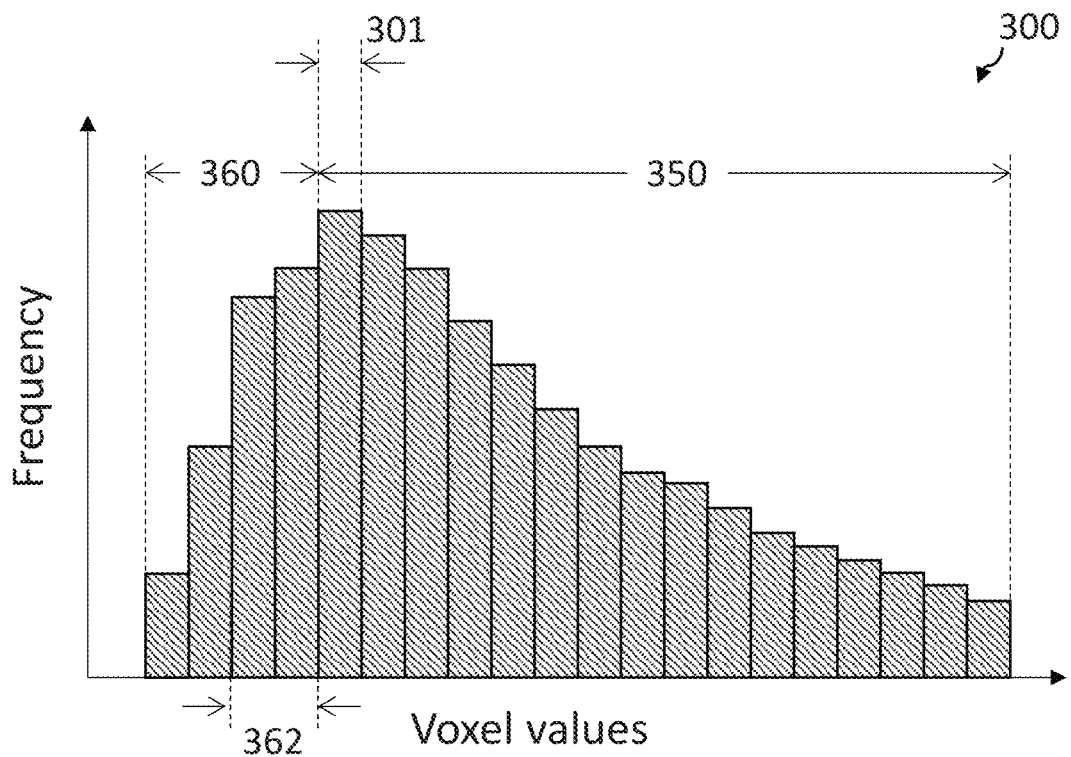
FIG. 3A shows a schematic representation of an example distribution of voxel values for first image data forming a portion of the 3D medical image data of FIG. 2.

FIG. 3A shows an example of a histogram 300 of image data corresponding to the first anatomical object 210 represented in FIG. 2. In this example, the anatomical object 210 is a bone. The histogram 300 represents, as vertical bars, the frequencies with which the voxel values of the selected first image data fall within given sub-ranges.

FIG. 3A represents schematically an example of the analysis process performed on the first image data selected by the selection process. The analysis process represented by FIG. 3A involves determining characteristics of the distribution of the voxel values of the first image data.

The characteristics of the first image data to be determined are based on the type of the anatomical object represented by the first image data, which in this case is bone. In this example, the particular characteristics of the image data which are determined are as described below. However, in other examples, for example, depending on the type of the anatomical object represented by a given portion of image data, a different one or more characteristics of the image data may be determined.

In the example shown in FIG. 3A, a first characteristic which is determined is an overall peak 301 in the distribution. In the example where the distribution is a distribution of Hounsfield units (HU), the peak of the histogram may occur around 300-330 HU, or typically around 320 HU. As described above, the actual voxel value of the peak may vary depending on various factors, such as, for example, the age of the patient being imaged.

A second characteristic of the distribution of voxel values which is determined is a range 350 of voxel values extending from a voxel value associated with the peak 301 to a maximum voxel value.

The range 350 of voxel values is the range of voxel values taken to represent the cortex. The maximum voxel value in the range 350 may be the maximum voxel value in the distribution of the first image data which has a frequency at or above a predetermined threshold frequency. For example, the maximum voxel value may be the maximum voxel value of the first image data with a non-zero frequency. In other examples, the maximum voxel value may be determined based on contextual information relating to the dataset. For example, the contextual information may indicate that a metal object or other object of high radiodensity is present and may also indicate that this object is represented in the first image data. In such cases, the maximum voxel value associated with the cortex of the bone may be set so as to exclude from the range 320 of voxel values corresponding with the cortex high voxel values which may correspond to other such objects of high radiodensity. This can prevent voxel values associated with objects which are not part of the cortex being visualised as if they were part of the cortex. In a typical example where the voxel values are measured in HU, the range 350 of voxel values determined to correspond to the cortex may extend from around 320 HU to around 950 HU. As described above, this range will differ between 3D medical image datasets, for example depending on the age of the patient being imaged or the particular type of the bone.

A third characteristic of the distribution of voxel values which is determined is a range 360 of voxel values extending from a minimum voxel value having a frequency at or above a predetermined threshold frequency to the voxel value associated with the peak 301. This range 360 of voxel values is associated with the marrow of the bone. In a typical example where the voxel values are measured in HU, this range may extend from around 250 HU to around 320 HU.

A fourth characteristic of the voxel values which is determined is a range 362 of voxel values within the range 360 which extends from the voxel value associated with the peak and in which the frequencies are at or above a predetermined proportion of the frequency at the peak 301. For example, the range 362 may comprise the range of voxel values immediately below the peak 301 which have frequencies within 70% of the frequency at the peak 301. In a typical example where the voxel values are measured in HU, this range may extend from around 290 to around 320 HU.

Figure 3B:
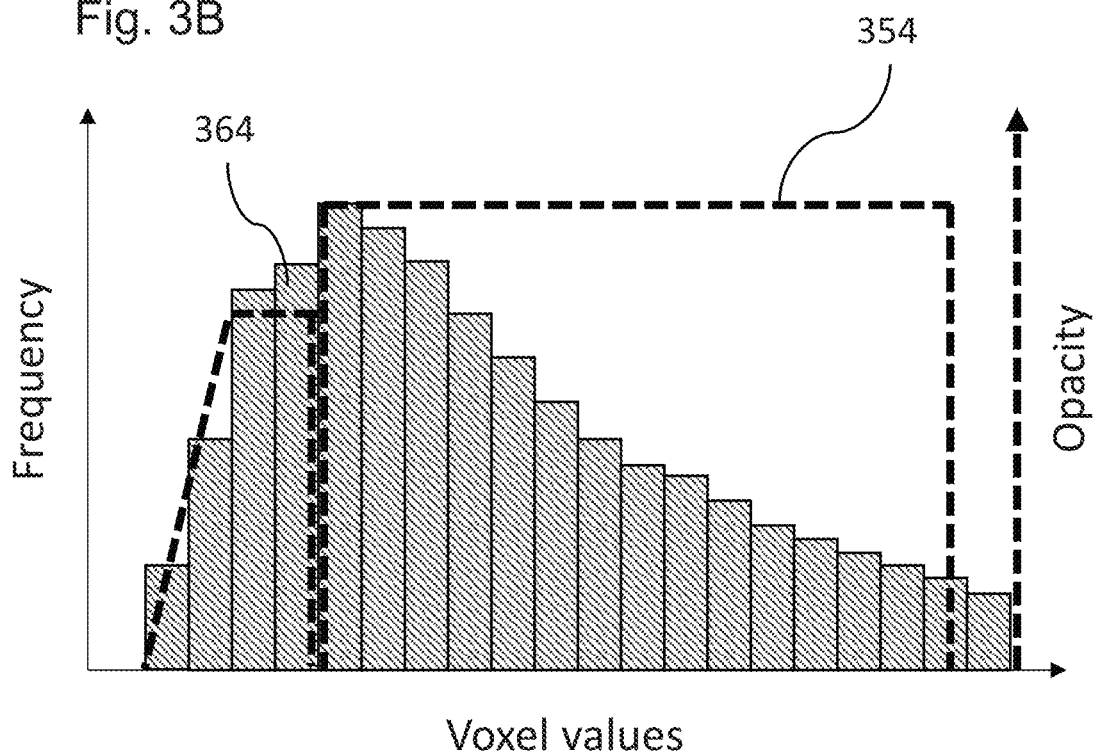
FIG. 3B shows a schematic representation of a determination of an example visual parameter mapping for the first image data of FIG. 3B.

FIG. 3B shows a schematic representation of how the results of the analysis process performed on the image data of FIG. 3A are used to determine a visual parameter mapping for the first image data to which the distribution corresponds, according to this example.

FIG. 3B shows the fitting of a function to the distribution. The form of the function which is fit to the first image data is determined by the fact that the first image data represents bone. The function which is fitted to the distribution comprises a rectangle 354 which is configured to extend over the range 320 of voxel values corresponding to cortex. The function also comprises a right trapezoid 364 which is configured to extend over the voxel values 360 corresponding to the marrow. The base of the trapezoid 364 extends over the entire range 360 while the upper side of the trapezoid 364 extends over the range 362 of voxel values having frequencies within a given proportion of the frequency at the peak 301.

According to this fitting, a transfer function is provided for the first image data. That is, voxel values which fall within the range 350 are mapped to an opacity value defined by the height of the rectangle 354, as represented by the vertical axis on the right-hand-side of FIG. 3B. In this example, each of the values determined to represent the cortex is mapped to the same opacity value, which is a maximum opacity value of, for example, 100%. A mapping of color values may be defined which may be configured to vary in any suitable manner with varying voxel value. For example, each of the voxel values falling in the range 350 representing the cortex may be assigned the same color value, or alternatively, the color value assigned for these values may vary with voxel value, for example, in order to convey information about the different radiodensities of different portions of the cortex. For example, colors assigned to points along the rectangle may ramp from a first predetermined color at a left side of the rectangle to a second pre-determined color at a right side of the rectangle. For example, the color assigned at a given point along the rectangle may be interpolated from the colors assigned at the left and right edges of the rectangle.

The transfer function defined according to the fitting to the distribution also provides a mapping to an opacity and a color for the range 360 of voxel values corresponding to the marrow. According to the applied fitting in tis example, the trapezoid 312 defines an opacity for this range 360 of voxel values which increases linearly from zero at the minimum voxel value in the range 360 to a maximum opacity at higher voxel values in the range. The maximum opacity for the range of voxel values 310 corresponding to the marrow may, for example, be 70% of the opacity which is applied by the rectangle 354 for the cortex range 350. In examples, the color assigned by the transfer function to the voxel values in the marrow region is different to the color assigned to the cortex region. As an example, red or orange colors may be assigned by the transfer function to voxels determined to represent marrow while white or grey colors may be assigned to voxels determined to represent cortex. The transfer function may also be defined such that a color assigned to voxel values in the marrow region varies with voxel value. For example, pre-determined colors may be assigned by different pre-determined relative points along the trapezoid in proportion to the width of the trapezoid. Accordingly, the actual voxel values to which these points along the trapezoid correspond, and thus to which the given colors are mapped, is determined by the above-described fitting of the trapezoid 364 to the image data.

The example shown in FIGS. 3A and 3B provides a transfer function for image data representing bone based on a particular set of characteristics of the image data, which are determined by the analysis process. In other examples, a different set of characteristics of the image data to those shown in FIGS. 3A and 3B could be determined in order to determine fit a transfer function for the image data. For example, some but not all of the characteristics described in relation to FIGS. 3A and 3B could be determined and a fitting could be determined based only on the determined characteristics. In other examples, further characteristics or an entirely different set of characteristics other than those shown in FIGS. 3A and 3B could be determined. In other examples, a different form of transfer function could be provided based on the results of the analysis of the image data. In such examples, the characteristics of the distribution of image data which are determined could be dependent on the form of the function to be fit to the distribution. For example, in an alternative example, a right-angle triangle, rather than a trapezoid, could be fit to the range of voxel values corresponding to marrow. In such an example, where a right-angle triangle is fit to the marrow region, there may be no need to determine the above-described fourth characteristic which defines the width of the upper side of the trapezoid. Furthermore, in another example, a trapezoid may be fit the marrow region of the distribution which is configured such that the upper side of the trapezoid has a length which is pre-determined proportion of the lower side of the trapezoid. For example, the upper side may have a width which is half the width of the lower side of the trapezoid. In such an example, there may also be no need to determine the above-described fourth characteristic of the voxel values.

Figure 4:
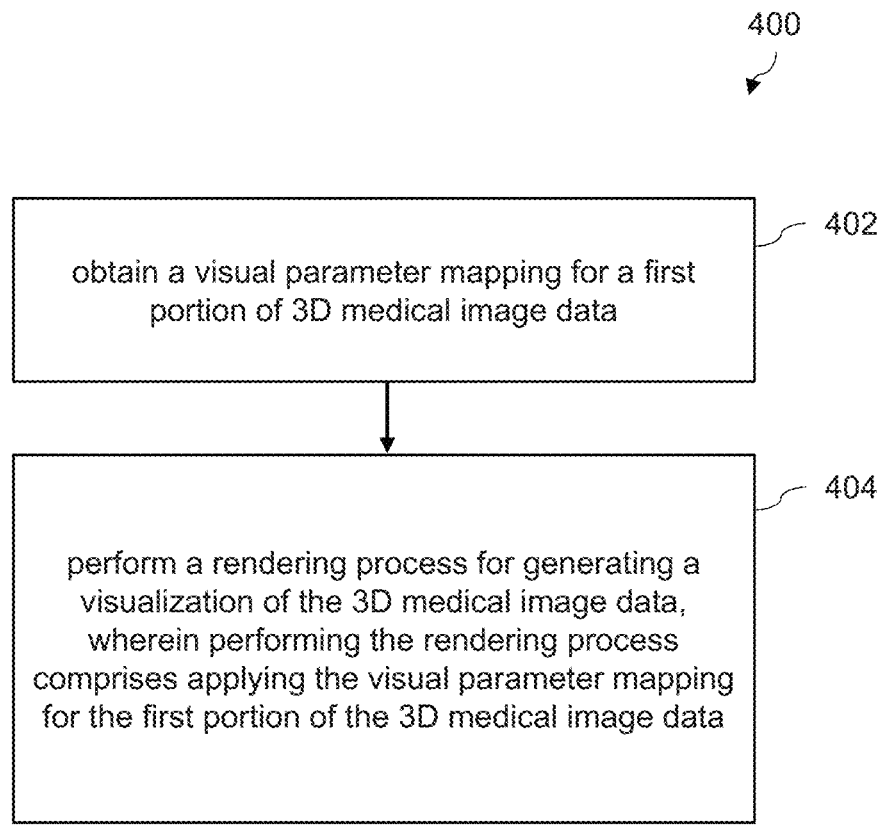
FIG. 4 shows a flowchart representation of a method for visualizing 3D medical image data according to an example of the present disclosure.

FIG. 4 shows a flowchart representation of an example method 400 of generating a computer-based visualization of 3D medical image data.

The method 400 comprises, at block 402, performing a method according to present disclosure to obtain a visual parameter mapping for a first portion of 3D medical image data.

In some examples, the process at block 402 may be performed a plurality of times for each of a plurality of different anatomical objects represented in the 3D medical image data. For example, the method described above for determining a visual parameter mapping for first image data in the 3D medical image data may be performed for multiple different portions of the 3D medical image data, each of the different portions comprising a respective different anatomical object. For example, with respect to the example image volume 200 of FIG. 2, a method according to FIG. 1 may be performed a first time to determine a first visual parameter mapping for a first portion of the 3D medical image data representing the first anatomical object 310, in this case bone, and a second time to determine a second visual parameter mapping for a second portion of the 3D medical image data representing a second anatomical object 320, e.g. the liver of the patient 10. Accordingly, two or more partial visual parameter mappings or partial transfer functions may be obtained for the volume 200, either or both of which may be applied in a rendering process for rendering a visualization of the volume 200.

At block 404, the method 400 comprises performing a rendering process for generating a visualization of the 3D medical image data, wherein performing the rendering process comprises applying the visual parameter mapping for the first portion of the 3D medical image data.

The rendering process may comprise any suitable volume rendering process. For example, the rendering process may be a direct volume rending process comprising defining a viewpoint with respect to the volumetric data and traversing a plurality of simulated rays originating at the viewpoint through the volumetric dataset. In such examples, each ray which is traversed through the volumetric dataset may allow determination of a value or set of values for display by a pixel of a viewing plane which is intersected by that ray. For example, a rendering algorithm may be employed which determines a value for display by the pixel via an integration of visual parameter values associated with sample points in the volume along the path of the ray.

It should be noted that at least some of the sample points may not be coincident with a voxel and as such calculations relating to a particular sample point, such as the above described visual parameter mapping or transfer function, may employ interpolation to determine a scalar value at that sample point. Trilinear interpolation, or another example method of interpolation, based on the scalar values of a set of voxels neighbouring the point may then be performed to determine an interpolated scalar value for a given sample point. Assigning a visual parameter to a given sample point may then comprise applying the visual parameter mapping to the interpolated value of the volumetric dataset at the sample point.

Various lighting effects may be applied in a given example rendering process. For example, a rendering process may model an illumination effect by modelling a light source illuminating the volume, for example by use of a light map.

Various volume data reconstruction filters may be used during rendering, e.g. nearest neighbour, trilinear or higher-order filters such as the B-spline filter. The filter may be interpolating or not. Where the filter is not interpolating, over-smoothing may be used as part of the rendering.

In some examples, data filtering may be applied separately from the rendering process. The data filtering may comprise, e.g., gaussian smoothing, unsharp masking, thresholding and various morphological operations.

According to examples of the present disclosure, the visual parameter mapping for at least a first portion of the volume representing a first anatomical object in the volume is assigned via an example of a method as described above. Portions of the volume which are not part of the first portion may be assigned a visual parameter mapping which is different to the mapping for the first portion. For example, by use of the selection process the volume may be segmented to form a plurality of segmentation masks. During rendering, the segmentation mask into which a given sample point falls may be used to determine the transfer function which is applied for the assigning visual parameter data at the sample point.

For example, in an example rendering process for visualizing the volume 200 of FIG. 2, the above-described method may be applied to determine a first visual parameter mapping for the bone 210 and a second visual parameter mapping for the liver 220. During rendering, in the example of a direct volume rendering process, the visual parameter mapping to be applied at a given sample point along a ray being traversed through the volume may be determined based on the portion of the volume 200 in which the sample point lies.

For example, assigning visual parameter data to a given sample point during rendering may comprise determining if the sample point lies in the first portion 210, the second portion 220, or outside of the first portion 210 and the second portion 220, and applying a visual parameter mapping based on this determination. In an example, this may be done by determining during rendering a segmentation mask to which a particular sample point belongs and applying the visual parameter mapping which is applicable for that segmentation mask. For example, if the sample point is determined to be within the first portion 210 the first visual parameter mapping is applied to determine visual parameter data for the sample point, while if the sample point is determined to be within the second portion 210 the second visual parameter mapping is applied. If the sample point is determined not to be within the first portion 210 or the second portion 220 a different visual parameter mapping may be applied.

An advantage of this approach is that a visual parameter mapping can be determined for individual portions of the 3D image data while a global visual parameter mapping may also be defined for the 3D image data as a whole. The global visual parameter mapping may be determined by manual adjustment by a user or by any other suitable means while a visual parameter mapping for specific anatomical objects can be determined according to methods described above. This means that the overall visual parameter mapping, determining which may in some examples be a time-consuming process, is not disturbed by the application of a local visual parameter mapping for a given portion of the data. Conversely, the local visual parameter mapping can be determined in an effective and efficient manner, as described above, by analyzing a portion of the image data which excludes image data which do not correspond to the given anatomical organ.

Figure 5:
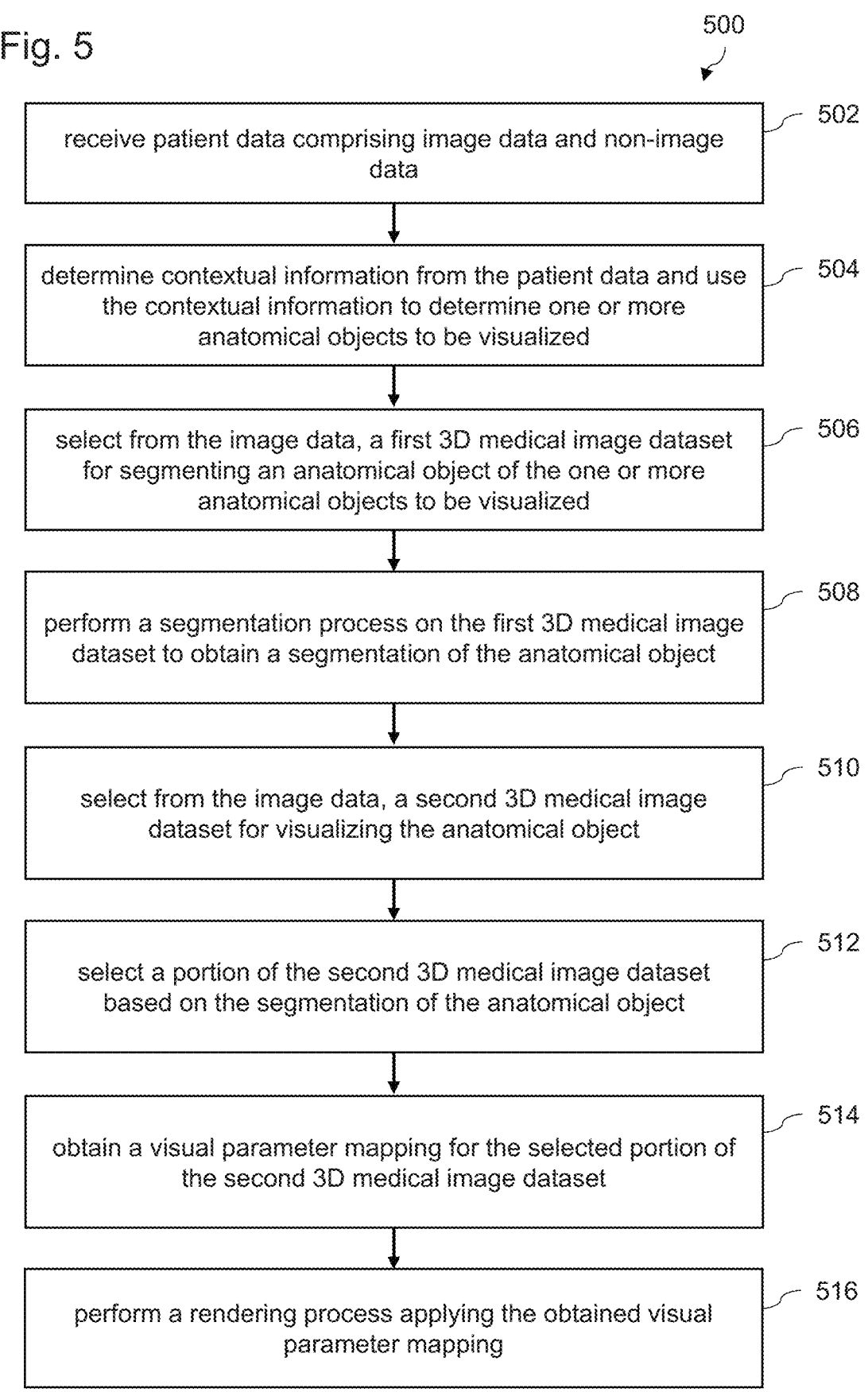
FIG. 5 shows a flowchart representation of a clinical workflow method according to an example of the present disclosure.

FIG. 5 shows a flowchart representation of an example clinical workflow method 500 comprising a method of rendering according to the example of FIG. 4.

At block 502, patient data is received which comprises image data and non-image data. The image data may comprise a plurality of 3D medical image datasets, for example representing the result of a plurality of medical scans of the patient obtained by one or more scanning methodologies and/or one or more scans obtained by one scanning methodology operating at different energy levels. Each of the 3D medical image datasets may show the same volume or different volumes of the patient.

At block 504, contextual information is determined from the patient data and is used to determine one or more anatomical objects to be visualized. The contextual information is indicative of the clinical use case for an image to be rendered from the image data. As described above, the clinical use case may be indicative of the organ to which the clinical use case relates. The clinical use case may additionally or alternatively be indicative of the stage of the patient in the clinical workflow. The contextual information may therefore be used to identify the information which should be conveyed to the user by the visualization. For example, the contextual information may be used to identify which organ, or which organs, should be included in the visualization and may additionally be used to determine the viewing angle, lighting conditions and any other factors which may influence the desired information to be conveyed to the user by the image to be rendered. The contextual information may be obtained in any suitable manner, examples of which have been described above.

At block 506, a first 3D medical image dataset for segmenting an anatomical object of the one or more anatomical objects to be visualized is selected from the image data. The first 3D medical image dataset may be selected as a dataset which is suitable for performing a segmentation thereon to segment the anatomical object. For example, if the contextual information obtained at block 504 indicates that the medical use case of the image to be rendered is to inspect the liver of the patient, then, at block 506, a first 3D medical image dataset which is suitable for segmenting the liver may be selected. For example, 3D medical image datasets obtained via a particular series or at a particular energy level may be more suitable for differentiating portions of the imaged volume represent the liver from those which do not represent the liver. In some examples, a factor which may affect which dataset is suitable for performing the segmentation is the level of filtering or smoothing which has been applied to the dataset. For example, a dataset in which filtering has not been applied to smooth voxel values, or on which only a moderate level of such filtering has been applied, may be more suitable for performing the segmentation than a dataset to which more smoothing has been applied. In some examples, the reconstruction kernel of a particular dataset may be indicative the level of smoothing which has been applied to the dataset.

At block 508, a segmentation process is performed on the first 3D medical image dataset to obtain a segmentation of the anatomical object. Examples of such a segmentation process have been described above.

At block 510, a second 3D medical image dataset is selected from the image data. The second 3D medical image is selected as a dataset to be used to render the visualization of the anatomical object. In some examples, the second 3D medical image dataset is different to the first 3D medical image dataset. For example, while a first 3D medical image dataset, e.g. a dataset obtained using a first imaging modality or using a first energy level, may be more suitable for segmenting the anatomical object, a second 3D medical image dataset, e.g. a dataset obtained using a different imaging modality or different energy level, may be determined to be more suitable for rendering a visualization of the anatomical object. The first and second 3D medical image datasets may, for example, be datasets obtained simultaneously. For example, the first and second 3D medical image datasets may be datasets representing results of a CT scan and may respectively represent results of a relatively low energy x-ray scan and a relatively high energy x-ray scan. In other examples, the first and second 3D medical image datasets may be datasets which are obtained using different imaging modalities or datasets belonging to different series obtained using the same imaging modality. In other examples, the first and second 3D medical image datasets used for the obtaining the segmentation and for visualizing the anatomical object may be the same dataset.

At block 512, a portion of the second 3D medical image dataset is selected based on the segmentation of the anatomical object obtained from the first 3D medical image dataset. For example, a segmentation of the region of the imaged volume representing the liver obtained from the first 3D medical image dataset may be applied to a second 3D medical image dataset to select a portion of the second 3D medical image dataset which represents the liver and which is to be used in a rendering process to visualize the liver. A registration between the first and second 3D medical image datasets may allow voxels in the dataset which correspond with the same point in the imaged volume to be identified. Thus, a segmentation of an anatomical object obtained by segmenting the first 3D medical image dataset may be applied to select a portion of the second 3D medical image dataset representing the same anatomical object. The steps performed at blocks 504 to 512 may, in some examples, be considered to form part of a selection process as described above, for selecting first image data for which to determine a visual parameter mapping.

At block 514, a visual parameter mapping is obtained for the selected portion of the second 3D medical image dataset. The visual parameter mapping is determined as described in examples above. The determining of a given visual parameter mapping, according to examples, is based on the contextual information wherein the contextual information determines a parameter of the analysis process which is performed on the portion of the image data to determine the visual parameter mapping for that portion.

Finally, at block 516, a rendering process is performed in which the visual parameter mapping obtained as described with reference to blocks 506 to 514 is applied. Examples of such a rendering process have been described above. In some examples, the steps described at blocks 506 to 514 are each performed a plurality of times in respect of different anatomical objects. For instance, if it is determined at block 504 that the visualization should show the liver and the skeleton of the patient, then blocks 506 to 514 may be performed to obtain a visual parameter mapping for the liver and performed again to obtain a visual parameter mapping for the skeleton. In such an example, at block 516, each of these obtained visual parameter mappings may be applied in the rendering process to visualize the respective anatomical objects to which the visual parameter mappings relate.

Different 3D medical image datasets may be used to obtain the segmentations and/or to visualize the different anatomical objects. For example, the above-described second 3D medical image dataset which is used to obtain the visual parameter mapping and to visualize a given anatomical object may be different for the different anatomical objects which are to be included in the visualization. Similarly, the above-described first 3D medical image dataset which is used to obtain a segmentation of the given anatomical object may be different for different anatomical objects to be included in the visualization. For example, the 3D medical image dataset or datasets used to segment and visualize the liver of the patient may be different to those used for the skeleton of the patient. In such an example, two or more respective rendered images of the different anatomical organs can be combined, for example by superimposing one image on the other, to provide a combined rendered image according to the clinical use case. Further, in some examples, two or more rendered images of a single anatomical object, obtained using different volumetric datasets may be used to render a combined image for the single anatomical object.

In some examples, a workflow according to the present disclosure may allow a user to alter the rendered image by, for example, selecting or deselecting given organs to be rendered. For example, the user could issue a voice command which could be used to select the organ or organs which are visualized.

Figure 6:
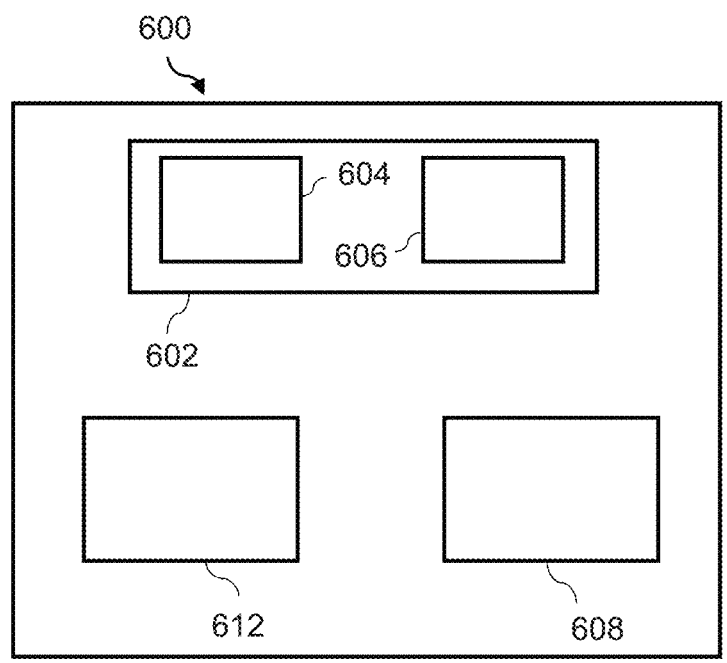
FIG. 6 illustrates schematically a system comprising a volume rendering apparatus, for performing certain example methods according to the present disclosure.

FIG. 6 illustrates schematically a system 600 for processing 3D medical image data. In the example shown, the system 600 comprises a computing device in the form of a computer 602. The computer 602 comprises one or more processors 604 and a memory 606. The memory 606 may be in the form of a computer readable storage medium. The memory 606 has stored on it instructions that, when executed by the one or more processors 604, cause the one or more processors to perform a method described above.

The instructions may be stored on the memory 606 when the system 600 is supplied to a user. Alternatively, the instructions may be provided to the user thereafter, for example in the form of a computer program product, e.g. via a computer readable storage medium such as a compact disk (CD), a digital versatile disk (DVD), hard disk drive, solid state drive, a flash memory device or the like. Alternatively, the instructions may be downloaded onto the storage medium 606 via a data communication network (e.g. the world-wide web).

In cases where the method carried out by the one or more processors 604 involves one or more neural networks, such neural networks may be stored on memory 606. As with the instructions stored on memory 606, the neural networks may be stored on the memory 606 when the system 600 is supplied to a user, or may be provided thereafter (e.g. in the form of a computer program product), whether via a computer readable storage medium, or via downloading the neural networks via a data communication network.

Particularly in cases where the method involves one or more neural networks, the one or more processors 604 may comprise one or more Graphics Processing Units (GPUs), for example, or other types of processors. The use of GPUs may optimize the system 600 for making use of neural networks. This is because, as will be appreciated, a GPU can handle a large number of threads at the same time.

As illustrated in FIG. 6, the system 600 may, in some examples, comprise one or more displays 612 for displaying to a user the view of the region of interest that was generated by the visualization process.

As also illustrated in FIG. 6, the system 600 may additionally comprise an imaging apparatus 608 configured to acquire the medical image data. For example, the system 600 may include an X-ray or MRI imaging apparatus.

In some examples, the system 600 may comprise an input interface such as a mouse, a keyboard (or respective connection interfaces for connecting same), a touch screen interface, a speech capturing device and the like. A user of the system 600 may use the input interface to input information into the system 600.

Although the invention has been described in the context of a direct volume rendering algorithm employing a ray casting approach, as mentioned above, it should be appreciated that the invention may be applied in other example methods of visualizing a volume. For example, the above described method of determining a composite representation of a volume and a surface may be used in other volume rendering techniques. For example, such methods may be employed in volume rendering techniques such as path tracing, splatting, or shear warp.

Although in certain examples described above, the visual parameter mapping has been described as a transfer function which maps voxel values to an opacity and a color, the visual parameter mapping may map voxel values to additional or alternative visual parameters. For example, in examples, a transfer function may be configured to assign one or more of: a scattering coefficient, a specular coefficient, a diffuse coefficient, a scattering distribution function, a bidirectional transmittance distribution function, a bidirectional reflectance distribution function, and colour information. These parameters may be used to derive a transparency, reflectivity, surface roughness, and/or other properties of the surface of the given point. These surface material properties may be derived based on scalar values of the volumetric dataset at the rendering location, and/or based on user-specified parameters.

Although in certain examples described above, the method involves determining the parameter of the analysis process based on the type of the anatomical object, such that, for example, the parameter of the analysis may be different depending on the type of the anatomical object, in other examples, the method may be specifically adapted for determining a visual parameter mapping for a single type of anatomical object. For example, the method may be provided as a set of computer-readable instructions configured to perform a method for selecting, from 3D medical image data, image data representing a given type of anatomical object, e.g. bone, and for performing on the image data an analysis process specifically adapted for determining a visual parameter mapping for the given type of object.

The above embodiments are to be understood as illustrative examples of the invention. Other embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The following points are also part of the disclosure:

1. Computer-implemented method for providing a visualization object for visualizing a three-dimensional anatomical region of a patient, which is represented by volume data (3D medical image data), for a user, including the steps of:
    calling/retrieving data assigned to the patient (in particular: from a database; the retrieved data in particular including non-image data);
    determining a medical context information item (or contextual information) based upon the assigned data;
    selecting suitable volume data of the patient based upon the medical context information item (from the available image data of the patient);
    based upon the medical context information item, identifying one or more structures (depicted in the selected volume data; another word for structure is anatomical object) to be visualized (in a visualization object for a user);
    determining a mapping rule for mapping the volume data on the visualization object, wherein the mapping rule is determined taking account of the medical context information item and/or the identified structures;
    calculating the visualization object based upon the mapping rule;
    providing the visualization object.

2. Method according to 1, wherein
    the identification is implemented based upon a segmentation of the volume data, wherein the segmentation is preferably implemented based upon the clinical context information item, and wherein, further preferably, the segmentation is a shape-based segmentation.

3. Method according to either of the preceding points, wherein
    the mapping rule has a partial mapping rule for each identified structure; and
    the determination step furthermore comprises:
        specifically adapting (or optimizing) the partial mapping rules for each identified structure, wherein the optimization for each partial mapping rule is implemented in particular independently of the respective other partial mapping rules.

4. Method according to 3, wherein
    the adaptation comprises an image-value-based or intensity-based adaptation or an adaptation in the intensity space and, in particular, an image-value-based or intensity-based segmentation or a segmentation in the intensity space.

5. Method according to 3 or 4, wherein
    the adaptation for each identified structure comprises:
        extracting an image information item from the volume data; and
        adapting the partial mapping rule based upon the image information item.

6. Method according to 5, wherein
    the image information item comprises a statistical frequency (or distribution) of image values of the volume pixels (voxels) belonging to the identified structure.

7. Method according to 6, wherein
    the volume data were at least partly generated using a computed tomography method; and
    the image information item comprises a statistical frequency (or distribution) of the Hounsfield units (HU).

8. Method according to any one of points 4 to 7, wherein
    the adaptation for each identified structure further comprises:
        determining at least two image information contributions in the image information item; and
        adapting the partial mapping rule based upon the image information contributions.

9. Method according to any one of points 4 to 8, wherein
    the adaptation for each identified structure further comprises:
        comparing the image information item with a reference image information item; and
        adapting the partial mapping rule based upon the comparison.

10. Method according to any one of points 3 to 9, wherein
    the adaptation of the partial mapping rules comprises:
        selecting a preset partial mapping rule assigned to the respective identified structure; and
        adapting the preset partial mapping rule in order to create the adapted partial mapping rule.

11. Method according to any one of points 3 to 10, wherein
    adapting the partial mapping rules is carried out based on the clinical context information item.

12. Method according to any one of points 3 to 11, wherein the partial mapping rules are adapted by applying a trained function that is embodied to specifically provide a partial mapping rule for each identified structure, in particular based upon the clinical context information item.

13. Method according to any one of the preceding points, wherein
the calculation is implemented using a volume rendering algorithm which, in particular, implements a method based on ray casting and/or path tracing; and
the mapping rule has one or more transfer functions.

14. Method according to any one of the preceding points, wherein
the mapping rule is embodied such that the identified structures are emphasized, in particular optically emphasized, for the user in the visualization object.

15. Method according to any one of the preceding points, wherein
the mapping rule comprises a global mapping rule, the global mapping rule defining one or more overarching scene properties of the visualization image.

16. Method according to any one of the preceding points, wherein
the mapping rule is embodied in such a way that the visualization object comprises a time-resolved sequence of a plurality of individual images.

17. Method according to 16, wherein
at least two of the individual images represent a different perspective of the volume data record.

18. Method according to any one of the preceding points, further including the step of:
receiving a user input in respect of the clinical context information item, wherein the clinical context information item is additionally determined based upon the user input.

19. Method according to any one of the preceding points, wherein
the selected volume data comprise a first volume data record which was recorded by a first imaging modality and comprise a second volume data record which was recorded by a second imaging modality that differs from the first; the method further comprising:
registering the first volume data record with the second volume data record; and
the step of determining the mapping rule further being additionally implemented based upon the registration.

20. Method according to any one of the preceding points, further including the steps of:
providing volume data relating to the patient; and
selecting the suitable volume data from the provided volume data.

21. Method according to any one of the preceding points, wherein the assigned data are called from a database or a plurality of different databases.

22. Computer-implemented method for providing a visualization object for visualizing a three-dimensional anatomical region of a patient, which is represented by 3D medical image data (or volume data), for a user, including the steps of:
providing the medical image data;
providing medical data assigned to the patient;
determining a medical context information item based upon the medical data and/or the medical image data;
based upon the medical context information item, identifying one or more structures (also denoted as anatomical object) in the selected volume data;
determining a mapping rule (also denoted as visual parameter mapping) for mapping the medical image data on a visualization object for a user, wherein the mapping rule comprises a partial mapping rule for each identified structure; and
the determination step furthermore comprises:
based upon the context information item and the medical image data, adapting the partial mapping rules specific to each identified structure;
calculating the visualization object based upon the mapping rule;
providing the visualization object for the user.

23. A computer-implemented method for providing a visualization object for visualizing a three-dimensional anatomical region of a patient, which is represented by volume data (also denoted as 3D medical image data), for a user, including the steps of:
receiving a selection command of the user, the selection command at least indicating the patient to be analyzed;
based upon the selection command, retrieving medical data assigned to the patient from a database;
determining a medical context information item (also denoted as contextual information) based upon the retrieved data;
selecting suitable volume data of the patient based upon the medical context information item and, optionally, the selection command;
based upon the medical context information item, identifying one or more structures (also denoted as anatomical object) comprised in the selected volume data to be visualized;
determining a mapping rule (also denoted as visual parameter mapping) for mapping the volume data on a visualization object for a user, wherein the mapping rule is determined based on the medical context information item and/or the identified structures;
calculating the visualization object based upon the mapping rule;
providing the visualization object for the user.

24. The method according to 23, wherein
the mapping rule comprises a partial mapping rule for each structure to be visualized; and
the determination step furthermore comprises:
specifically adapting the partial mapping rules for each structure to be visualized, wherein the adaptation of each partial mapping rule is, in particular, implemented independently of the respective other partial mapping rules.

25. The method according to 24, wherein
the adaptation for each structure to be visualized comprises:
extracting an image information item from the volume data, in particular, from the volume data associated with the respective structure to be visualized; and
adapting the partial mapping rule based upon the image information item, in particular, by analyzing the image information item.

26. The method according to 25, wherein
the image information item comprises a statistical frequency (or distribution) of voxel values and/or intensity values of the volume pixels belonging to the structure to be visualized.

27. The method according to 25 and/or 26, wherein
the adaptation for each structure to be visualized further comprises:
determining at least two different image information contributions in the image information item; and adapting the partial mapping rule based upon the image information contributions.

28. The method according to any one of the preceding points, wherein
the calculation is implemented using a volume rendering algorithm which, in particular, implements a method based on ray casting and/or path tracing; and
the mapping rule has one or more transfer functions.

29. The method according to any one of the preceding points, further including the step of:
receiving a user input in respect of the clinical context information item, wherein the clinical context information item is additionally determined based upon the user input.

30. The method according to any one of the preceding points, wherein
the selected volume data comprise a first volume data record (3D medical image data set) which was recorded by a first imaging modality and comprise a second volume data record (3D medical image data set) which was recorded by a second imaging modality that differs from the first; the method further comprising:
registering the first volume data record with the second volume data record; and
the step of determining the mapping rule further being additionally implemented based upon the registration.

31. A system for providing a visualization object which visualizes a three-dimensional anatomy of a patient, which is represented by medical volume data, for a user, comprising:
an interface for receiving a selection command of the user, the selection command indicating the patient to be analyzed, and for receiving medical volume data; and
a computing unit which is embodied:
to receive and/or call based upon the selection command data assigned to the patient (from a database);
to determine based upon the assigned data a medical context information item;
to select based upon the medical context information item and, optionally, the selection command, suitable volume data of the patient (from the image data available for the patient);
to identify based upon the medical context information item one or more structures to be visualized in the selected volume data;
to determine based upon the medical context information item and/or the structures to be visualized a mapping rule for mapping the volume data on a visualization object for a user;
to calculate the visualization object based upon the mapping rule; and
to provide the visualization object for the user.

32. A computer-implemented method for providing a visualization object for visualizing a three-dimensional anatomical region of a patient, which is represented by volume data, for a user, including the steps of:
providing the volume data;
providing context data assigned to the patient, which differ from the volume data;
determining a medical context information item based upon the assigned context data;
based upon the medical context information item, identifying one or more structures to be visualized in the selected volume data;
determining a mapping rule for mapping the volume data on a visualization object for a user, wherein
the mapping rule has a partial mapping rule for each identified structure;
the determination step furthermore comprises:
based upon the context information item, adapting the partial mapping rules specific to each identified structure; and
adapting for each structure comprises an extraction of an image information item from the volume data associated with the respective structure and an adaptation of the partial mapping rule based upon the image information;
calculating the visualization object based upon the mapping rule;
providing the visualization object for the user.

33. Computer program product having a computer program which is directly loadable into a memory of a visualization system, comprising program sections to carry out all steps of the method for visualizing a three-dimensional object according to any one of the preceding points and/or as claimed in any one of the following claims when the program sections are executed by the visualization system.

34. Computer-readable storage medium, on which program sections that are readable and executable by a visualization system are stored, in order to carry out all steps of the method for visualizing a three-dimensional object according to any one of the preceding points and/or as claimed in any one of the following claims when the program sections are executed by the visualization system.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for use in generating a computer-based visualization of 3D medical image data, the method comprising:
performing a selection process to select first image data forming a first portion of 3D medical image data, the first image data representing a first anatomical object of a type, the 3D medical image data including a plurality of 3D medical image datasets, and the selection process including
selecting a first 3D medical image dataset among the plurality of 3D medical image datasets,
identifying a portion of the first 3D medical image dataset representing the first anatomical object,
selecting a second 3D medical image dataset among the plurality of 3D medical image datasets, and
selecting the first image data from the second 3D medical image dataset based on the portion of the first 3D medical image dataset;
performing an analysis process on the first image data, a parameter of the analysis process being based on the type of the first anatomical object; and
determining a visual parameter mapping for the first portion based on a result of the analysis process, the visual parameter mapping being for use in a rendering process for generating the computer-based visualization of the 3D medical image data.

2. The method of claim 1, wherein the performing the analysis process comprises determining one or more characteristics of the first image data based on the parameter of the analysis process.

3. The method of claim 2 wherein
the one or more characteristics of the first image data include one or more characteristics of a distribution of first voxel values of the first image data; and
the performing the analysis process comprises analyzing the distribution of the first voxel values to determine the one or more characteristics of the distribution.

4. The method of claim 3, wherein the one or more characteristics of the distribution comprise a voxel value or a range of voxel values which satisfy a criterion.

5. The method of claim 4, wherein the criterion defines a voxel value or a range of voxel values associated with a local or global maximum in the distribution.

6. The method of claim 3, wherein the determining the visual parameter mapping comprises determining a function defining the visual parameter mapping based on the result of the analysis process.

7. The method of claim 2, wherein the determining the visual parameter mapping comprises determining a function defining the visual parameter mapping based on the result of the analysis process.

8. The method of claim 2, further comprising:
determining the parameter of the analysis process based on the type of the first anatomical object.

9. The method of claim 2, wherein a parameter of the selection process is based on the type of the first anatomical object represented by the first image data.

10. The method of claim 2, wherein the parameter of the selection process is determined based on contextual information relating to the 3D medical image data.

11. The method of claim 2, wherein the parameter of the analysis process is determined based on contextual information relating to the 3D medical image data.

12. The method of claim 1, further comprising:
determining the parameter of the analysis process based on the type of the first anatomical object.

13. The method of claim 1, wherein a parameter of the selection process is based on the type of the first anatomical object represented by the first image data.

14. The method of claim 1, wherein the parameter of the selection process is determined based on contextual information relating to the 3D medical image data.

15. The method of claim 14, wherein the contextual information relating to the 3D medical image data is one or more of:
textual information identifying a medical context of the 3D medical image data; or
medical history information associated with the 3D medical image data.

16. The method of claim 1, wherein the parameter of the analysis process is determined based on contextual information relating to the 3D medical image data.

17. The method of claim 16, wherein the contextual information relating to the 3D medical image data is one or more of:
textual information identifying a medical context of the 3D medical image data; or
medical history information associated with the 3D medical image data.

18. The method of claim 1, wherein the visual parameter mapping is a transfer function for use in a volume rendering process.

19. The method according to claim 18, wherein the transfer function is configured to provide at least one of opacity values or color values for the first image data, the at least one of opacity values or color values being for use in the volume rendering process.

20. The method of claim 1, wherein the first anatomical object includes an anatomical organ.

21. A method of generating a computer-based visualization of 3D medical image data, the method comprising:
performing the method of claim 1 to obtain a visual parameter mapping for a first portion of 3D medical image data; and
performing a rendering process for generating the computer-based visualization of the 3D medical image data, the performing the rendering process including applying the visual parameter mapping for the first portion of the 3D medical image data.

22. A non-transitory machine-readable medium storing a set of machine-readable instructions which, when executed by at least one processor, configure the at least one processor to perform the method of claim 21.

23. A non-transitory machine-readable medium storing a set of machine-readable instructions which, when executed by at least one processor, configure the at least one processor to perform the method of claim 1.

24. The method of claim 2, wherein the visual parameter mapping is a transfer function for use in a volume rendering process.

25. An apparatus, comprising:
one or more processors; and a storage storing a set of machine-readable instructions which, when executed by the one or more processors, cause the one or more processors to
perform a selection process to select first image data forming a first portion of 3D medical image data, the first image data representing a first anatomical object of a type, the 3D medical image data including a plurality of 3D medical image datasets, and the selection process including
selecting a first 3D medical image dataset among the plurality of 3D medical image datasets,
identifying a portion of the first 3D medical image dataset representing the first anatomical object,
selecting a second 3D medical image dataset among the plurality of 3D medical image datasets, and
selecting the first image data from the second 3D medical image dataset based on the portion of the first 3D medical image dataset,
perform an analysis process on the first image data, a parameter of the analysis process being based on the type of the first anatomical object, and
determine a visual parameter mapping for the first portion based on a result of the analysis process, the visual parameter mapping being for use in a rendering process for generating a computer-based visualization of the 3D medical image data.

26. A method of generating a computer-based visualization of 3D medical image data, the method comprising:
performing a selection process to select first image data forming a first portion of 3D medical image data, the first image data representing a first anatomical object of a type;
performing an analysis process on the first image data, a parameter of the analysis process being based on the type of the first anatomical object;
determining a visual parameter mapping for the first portion based on a result of the analysis process, the visual parameter mapping being for use in a rendering process for generating the computer-based visualization of the 3D medical image data; and
performing a rendering process for generating the computer-based visualization of the 3D medical image data, the performing the rendering process including applying the visual parameter mapping for the first portion of the 3D medical image data.

27. The method of claim 26, wherein the performing the analysis process comprises determining one or more characteristics of the first image data based on the parameter of the analysis process.

* * * * *